United States Patent
Fielding et al.

(10) Patent No.: US 8,403,961 B2
(45) Date of Patent: Mar. 26, 2013

(54) METHODS AND DEVICES FOR CONTROLLED FLEXION RESTRICTION OF SPINAL SEGMENTS

(75) Inventors: Louis Fielding, San Carlos, CA (US); Ian Bennett, San Francisco, CA (US); Manish Kothari, San Rafael, CA (US); Todd Alamin, Woodside, CA (US); Hugues Malandain, Mountain View, CA (US); Craig Litherland, Palo Alto, CA (US); Colin Cahill, San Francisco, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 1300 days.

(21) Appl. No.: 12/106,103

(22) Filed: Apr. 18, 2008

(65) Prior Publication Data

US 2008/0319487 A1    Dec. 25, 2008

Related U.S. Application Data

(60) Provisional application No. 60/936,897, filed on Jun. 22, 2007.

(51) Int. Cl.
*A61B 17/70* (2006.01)

(52) U.S. Cl. .................. 606/263; 606/246; 606/248

(58) Field of Classification Search .............. 606/279, 606/60–278; 623/17.11–17.16
See application file for complete search history.

(56) References Cited

U.S. PATENT DOCUMENTS

| | | | |
|---|---|---|---|
| 3,648,691 A | 3/1972 | Lumb et al. | |
| 4,246,660 A | 1/1981 | Wevers | |
| 4,643,178 A | 2/1987 | Nastari et al. | |
| 4,708,132 A | 11/1987 | Silvestrini | |
| 4,743,260 A | 5/1988 | Burton | |
| 4,772,286 A | 9/1988 | Goble et al. | |
| 4,776,851 A | 10/1988 | Bruchman et al. | |
| 4,794,916 A | 1/1989 | Porterfield et al. | |
| 4,870,957 A | 10/1989 | Goble et al. | |
| 4,955,910 A | 9/1990 | Bolesky | |
| 4,966,600 A | 10/1990 | Songer et al. | |
| 5,002,574 A | 3/1991 | May et al. | |
| 5,011,484 A * | 4/1991 | Breard | 606/249 |
| 5,011,494 A | 4/1991 | von Recum et al. | |
| 5,092,866 A | 3/1992 | Breard et al. | |
| 5,108,433 A | 4/1992 | May et al. | |

(Continued)

FOREIGN PATENT DOCUMENTS

| | | |
|---|---|---|
| EP | 0 322 334 A1 | 6/1989 |
| EP | 0 743 045 A2 | 11/1996 |

(Continued)

OTHER PUBLICATIONS

Al Baz et al., "Modified Technique of Tension Band Wiring in Flexion Injuries of the Middle and Lower Cervical Spine," Spine, vol. 20, No. 11, 1995, p. 1241-1244.

(Continued)

*Primary Examiner* — Eduardo C Robert
*Assistant Examiner* — James Palmer
(74) *Attorney, Agent, or Firm* — Wilson, Sonsini, Goodrich & Rosati

(57) ABSTRACT

A system for restricting spinal flexion includes superior and inferior tether structures joined by a pair of compliance members. Compliance members comprise tension members which apply a relatively low elastic tension on the tether structures. By placing the tether structures on or over adjacent spinous processes, flexion of a spinal segment can be controlled in order to reduce pain.

8 Claims, 19 Drawing Sheets

U.S. PATENT DOCUMENTS

| | | |
|---|---|---|
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,395,374 A | 3/1995 | Miller et al. |
| 5,415,658 A | 5/1995 | Kilpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,609,634 A * | 3/1997 | Voydeville .................. 623/13.11 |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A * | 3/1998 | Bevan et al. .................. 606/263 |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 * | 6/2003 | Yun ................ 606/249 |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,835,207 B2 | 12/2004 | Zacouto et al. |
| 6,899,716 B2 | 5/2005 | Cragg et al. |
| 6,946,000 B2 | 9/2005 | Senegas |
| 7,029,475 B2 | 4/2006 | Panjabi |
| 7,087,083 B2 | 8/2006 | Pasquet et al. |
| 7,101,398 B2 | 9/2006 | Dooris et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,335,200 B2 | 2/2008 | Carli |
| 7,413,576 B2 | 8/2008 | Sybert et al. |
| 7,445,637 B2 | 11/2008 | Taylor |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow et al. |
| 7,553,320 B2 | 6/2009 | Molz, IV et al. |
| 7,559,951 B2 | 7/2009 | DiSilvestro et al. |
| 7,591,837 B2 | 9/2009 | Goldsmith |
| 7,608,094 B2 | 10/2009 | Falahee |
| 7,686,832 B2 | 3/2010 | Jackson |
| 7,837,688 B2 * | 11/2010 | Boyer et al. .................. 606/86 A |
| 8,092,535 B2 | 1/2012 | Zucherman et al. |
| 2002/0095154 A1 | 7/2002 | Atkinson et al. |
| 2002/0147449 A1 | 10/2002 | Yun |
| 2002/0151978 A1 | 10/2002 | Zacouto et al. |
| 2003/0088251 A1 | 5/2003 | Braun et al. |
| 2004/0024458 A1 | 2/2004 | Senegas et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0122427 A1* | 6/2004 | Holmes .......................... 606/61 |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0215341 A1 | 10/2004 | Sybert et al. |
| 2004/0243239 A1 | 12/2004 | Taylor |
| 2005/0033435 A1 | 2/2005 | Belliard et al. |
| 2005/0049708 A1* | 3/2005 | Atkinson et al. .......... 623/17.16 |
| 2005/0123581 A1 | 6/2005 | Ringeisen et al. |
| 2005/0131405 A1 | 6/2005 | Molz, IV et al. |
| 2005/0154390 A1 | 7/2005 | Biedermann et al. |
| 2005/0192581 A1 | 9/2005 | Molz et al. |
| 2005/0216017 A1* | 9/2005 | Fielding et al. ................ 606/74 |
| 2005/0245930 A1 | 11/2005 | Timm et al. |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1* | 3/2006 | Zucherman et al. ....... 623/17.11 |
| 2006/0069471 A1 | 3/2006 | DiSilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0016303 A1 | 1/2007 | Jackson |
| 2007/0073293 A1 | 3/2007 | Martz et al. |
| 2007/0083200 A1 | 4/2007 | Gittings et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 * | 10/2008 | Bennett et al. ................ 606/263 |
| 2008/0281423 A1 | 11/2008 | Sheffer et al. |
| 2008/0312693 A1 | 12/2008 | Trautwein et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |

| | | | |
|---|---|---|---|
| 2009/0264932 | A1 | 10/2009 | Alamin et al. |
| 2009/0270918 | A1 | 10/2009 | Attia et al. |
| 2010/0004701 | A1 | 1/2010 | Malandain et al. |
| 2010/0023060 | A1* | 1/2010 | Bennett et al. ............... 606/263 |
| 2010/0036424 | A1 | 2/2010 | Fielding et al. |
| 2010/0234890 | A1 | 9/2010 | Alamin et al. |
| 2010/0234894 | A1 | 9/2010 | Alamin et al. |
| 2010/0249839 | A1 | 9/2010 | Alamin et al. |
| 2011/0125191 | A1 | 5/2011 | Boyer et al. |
| 2011/0295322 | A1 | 12/2011 | Fielding et al. |

FOREIGN PATENT DOCUMENTS

| | | | |
|---|---|---|---|
| EP | 0743045 | A3 | 12/1996 |
| EP | 1 994 901 | A1 | 11/2008 |
| FR | 2 681 525 | A1 | 3/1993 |
| FR | 2 714 591 | | 7/1995 |
| FR | 2 717 675 | A1 | 9/1995 |
| FR | 2 828 398 | A1 | 2/2003 |
| FR | 2 851 154 | | 8/2004 |
| FR | 2 874 167 | A1 | 2/2006 |
| FR | 2 884 136 | A1 | 10/2006 |
| JP | 10-277070 | | 10/1998 |
| JP | 2008-514289 | | 5/2008 |
| JP | 2008-540055 | | 11/2008 |
| WO | WO 01/28442 | | 4/2001 |
| WO | WO 02/03882 | A2 | 1/2002 |
| WO | WO 02/03882 | A3 | 5/2002 |
| WO | WO 02/051326 | | 7/2002 |
| WO | WO 02/071960 | | 9/2002 |
| WO | WO 03/0452662 | | 6/2003 |
| WO | WO 03/045262 | A3 | 1/2004 |
| WO | WO 2004/052246 | | 6/2004 |
| WO | WO 2004/073532 | | 9/2004 |
| WO | WO 2004/073533 | | 9/2004 |
| WO | WO 2005/087168 | A2 | 9/2005 |
| WO | WO 2005/110258 | A1 | 11/2005 |
| WO | WO 2005/112835 | A2 | 12/2005 |
| WO | WO 2005/087168 | A3 | 1/2006 |
| WO | WO 2005/112835 | A3 | 2/2007 |
| WO | WO 2008/051423 | | 5/2008 |
| WO | WO 2008/051801 | | 5/2008 |
| WO | WO 2008/051802 | | 5/2008 |
| WO | WO 2008/051806 | | 5/2008 |
| WO | WO 2008/051802 | A3 | 7/2008 |
| WO | WO 2008/051806 | A3 | 7/2008 |
| WO | WO 2008/051801 | A3 | 8/2008 |
| WO | WO 2009/149407 | | 12/2009 |
| WO | WO 2009/149407 | A9 | 12/2009 |
| WO | WO 2010/028165 | | 3/2010 |
| WO | WO 2010/028165 | A8 | 10/2010 |

OTHER PUBLICATIONS

Dickman et al., "Comparative Mechanical Properties of Spinal Cable and Wire Fixation Systems," Spine, vol. 22, No. 6, Mar. 15, 1997, pp. 596-604.

Garner et al., "Development and Preclinical Testing of a New Tension-Band Device for the Spine: the Loop system," European Spine Journal, vol. 11 (Suppl 2), 2002, pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000, pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000, pp. 489-495.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Biomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

International Search Report and Written Opinion of PCT Application No. PCT/US2007/022191, dated Mar. 14, 2008, 13 pages total.

International Search Report and Written Opinion of PCT Application No. PCT/US2007/081835, dated Mar. 24, 2008, 8 pages.

International Search Report and Written Opinion of PCT Application No. PCT/US2007/081822, dated May 8, 2008, 10 pages total.

U.S. Appl. No. 11/777,366, filed Jul. 13, 2007; first named inventor: Todd Alamin.

Frymoyer et al., "An Overview of the Incidence and Costs of Low Back Pain" Orthrop. Clin. North Am., 1991;22: 263-271.

Abbott Spine, Wallis Surgical Technique [Product Brochure], 2006; 24 pages total.

Medtronic Sofamor Danek USA, Inc., DIAM™ System Implant; 2006 [Product Brochure]; downloaded from the Internet: <http://spineinfo.ru/~files/DIAMST.pdf>, 20 pages total.

International Search Report and Written Opinion of PCT Application No. PCT/US2007/081815, dated Jun. 23, 2008, 10 pages.

International Search Report and Written Opinion of PCT Application No. PCT/US08/60908, dated Sep. 3, 2008.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

U.S. Appl. No. 13/073,620, filed Mar. 28, 2011, Fielding et al.

International search report and written opinion dated Oct. 4, 2010 for PCT/US2010/044300.

European search report and search opinion dated Dec. 4, 2012 for Application No. 8746344.4.

* cited by examiner

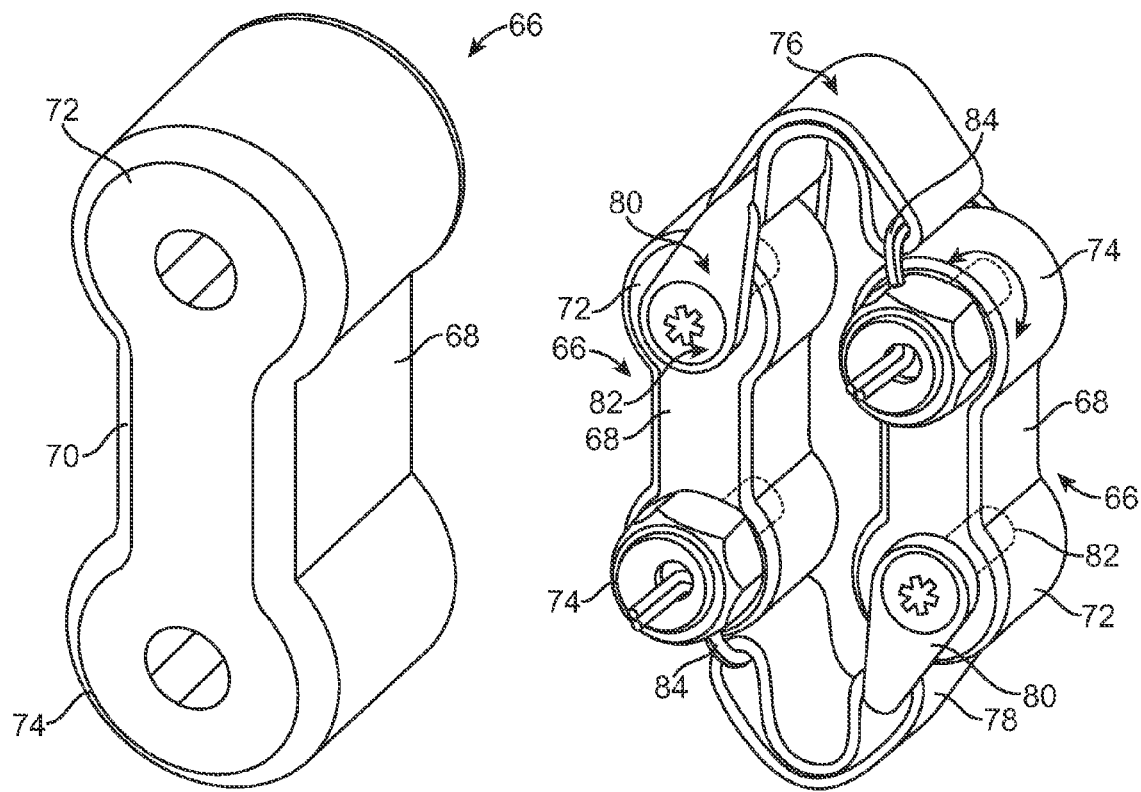
FIG. 7A
FIG. 7B
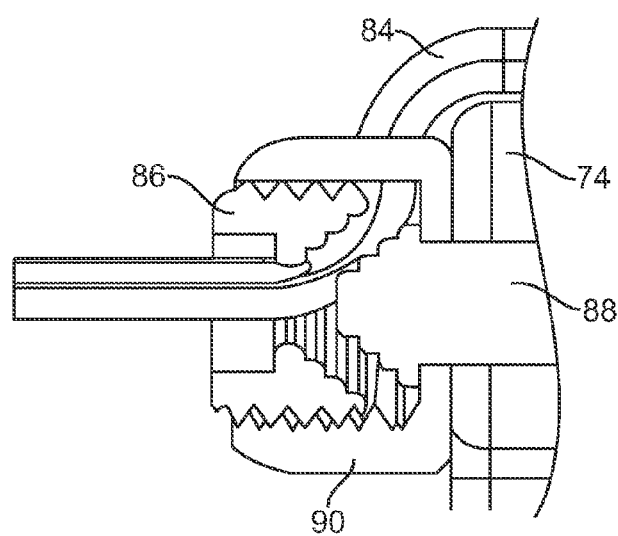
FIG. 7C

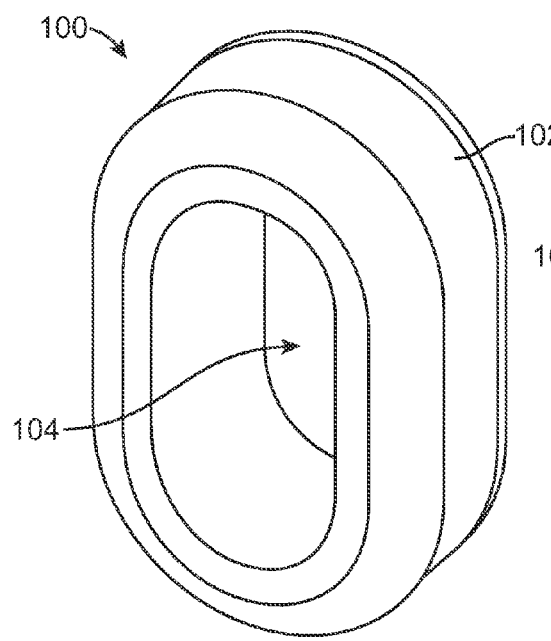
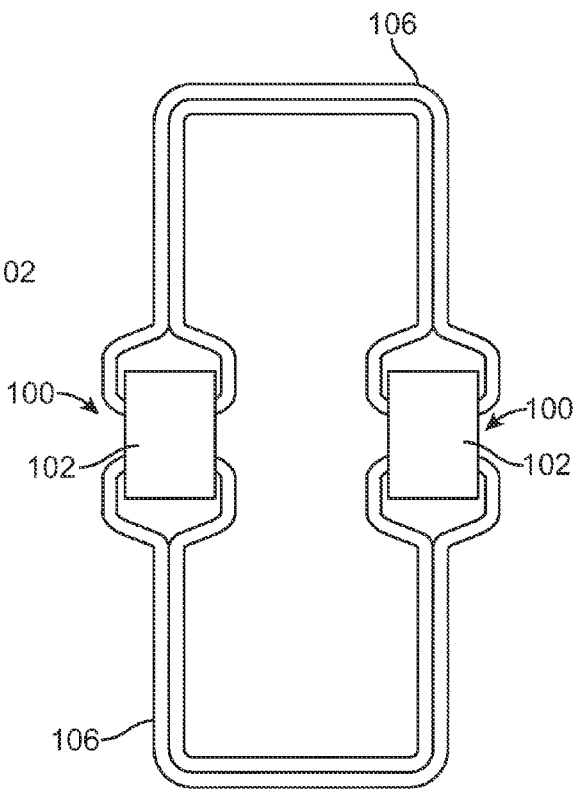
FIG. 8A  FIG. 8B
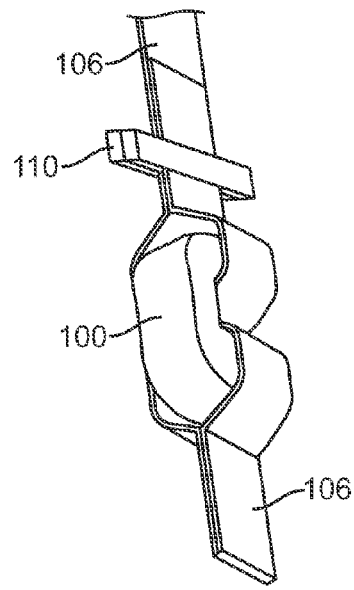
FIG. 8C

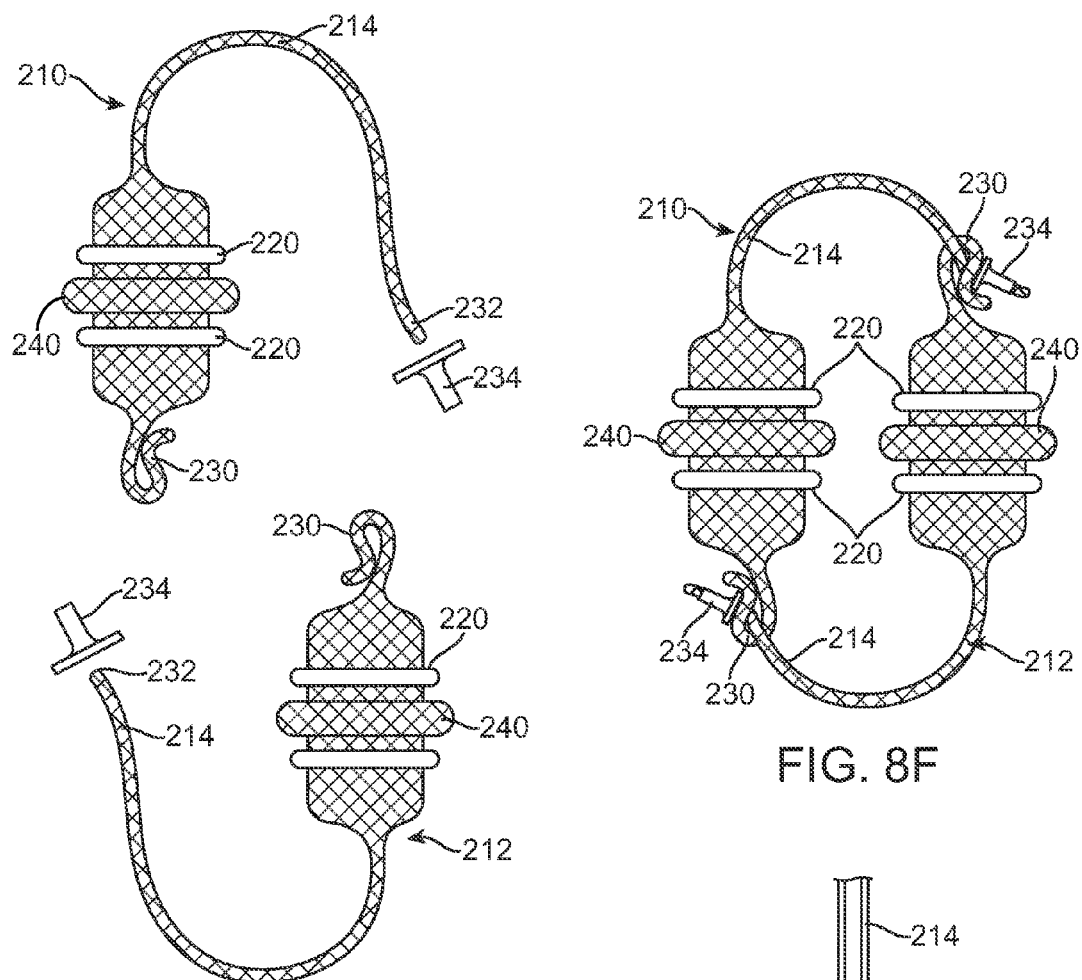
FIG. 8E
FIG. 8F
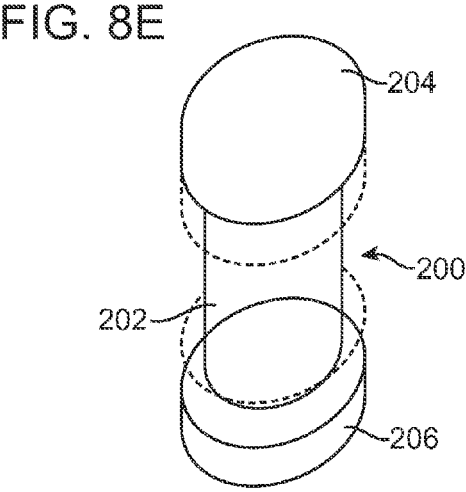
FIG. 8D
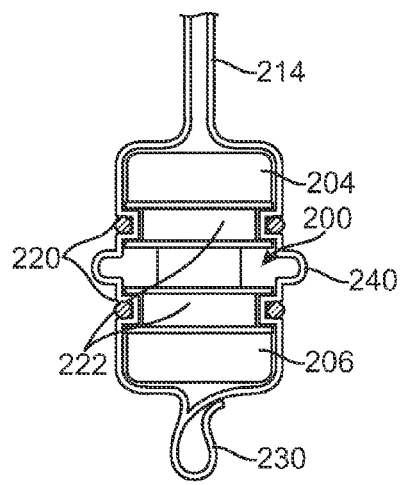
FIG. 8G

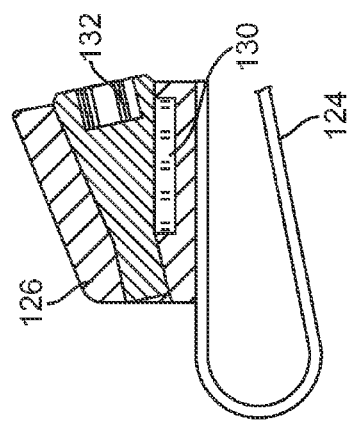
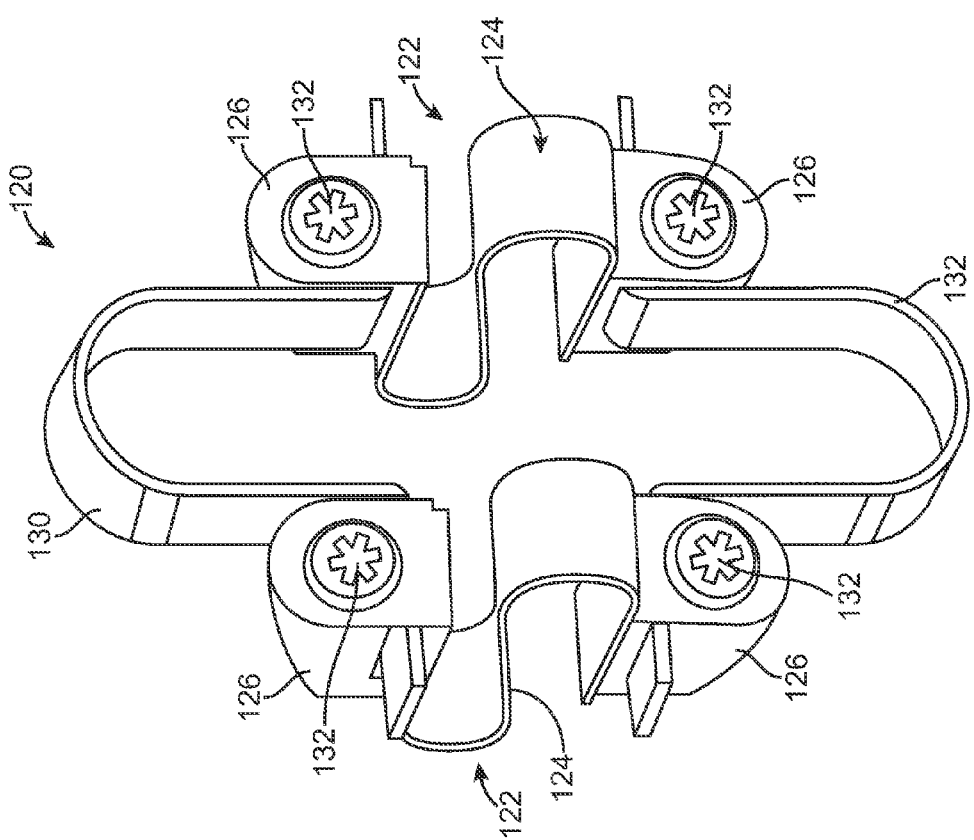

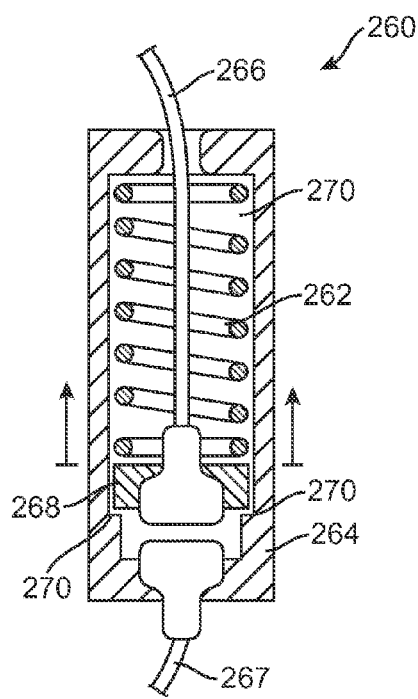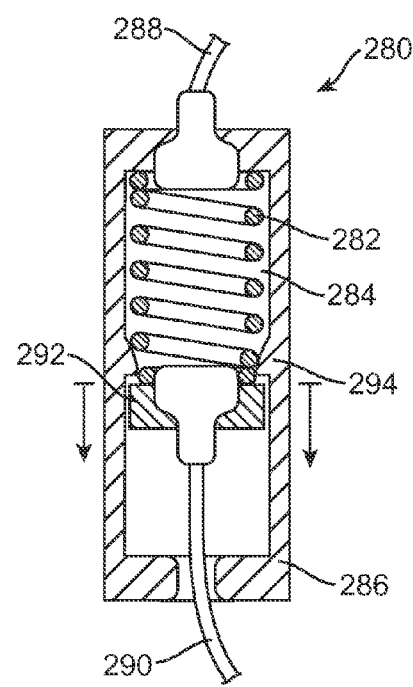
FIG. 14A    FIG. 14B
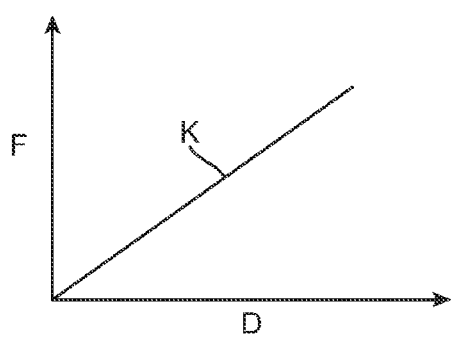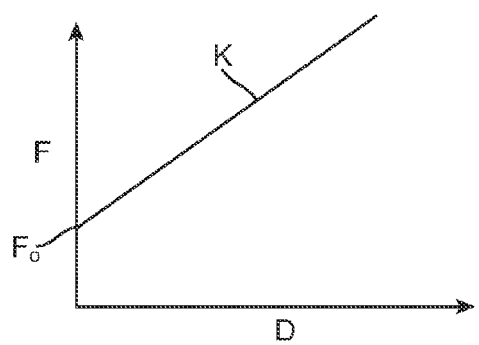
FIG. 15A    FIG. 15B

METHODS AND DEVICES FOR CONTROLLED FLEXION RESTRICTION OF SPINAL SEGMENTS

CROSS-REFERENCES TO RELATED APPLICATIONS

This application claims the benefit of prior provisional application 60/936,897, filed on Jun. 22, 2007, the full disclosure of which is incorporated herein by reference.

The present invention is related to but does not claim priority from application Ser. No. 11/076,469, filed on Mar. 9, 2005, which claimed the benefit of prior provisional application 60/551,235, filed on Mar. 9, 2004; application Ser. No. 11/777,366; filed on Jul. 13, 2007; application Ser. No. 11/827,980; filed on Jul. 13, 2007; PCT application no. US 2007/081815; filed on Oct. 18, 2007; PCT application no. US 2007/081822; filed on Oct. 18, 2007; and application Ser. No. 11/975,674; filed on Oct. 19, 2007, the full disclosures of which are incorporated herein by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the lower lumbar discs of the spine (FIG. 1). Pain is typically exacerbated when patients put their lumbar spines into flexion (i.e. by sitting or bending forward) and relieved when they put their lumbar spines into extension (i.e. the standing position, or arching backwards). Discogenic pain can be quite disabling, and for some patients, can dramatically affect their ability to work and otherwise enjoy their lives.

Such discogenic low back pain can be thought of as flexion instability and is related to flexion instability that is manifested in other conditions. The most prevalent of these is spondylolisthesis, a spinal condition in which abnormal segmental translation is exacerbated by segmental flexion.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebrae. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

An alternative method, that is not commonly used in practice, but has been approved for use by the FDA, is the application of bone cerclage devices that can encircle the spinous processes or other vertebral elements and thereby create a restraint to motion. Physicians typically apply a tension or elongation to the devices that applies a constant and high force on the anatomy, thereby fixing the segment in one position and allowing effectively no motion. The lack of motion allowed after the application of such a device is thought useful to improve the likelihood of fusion performed concomitantly; if the fusion does not take, these devices will fail through breakage of the device or of the spinous process to which the device is attached. These devices are designed for static applications and are not designed to allow for a dynamic elastic resistance to flexion across a range of motion. The purpose of bone cerclage devices and the other techniques described above is to almost completely restrict measurable motion of the vertebral segment of interest. This loss of motion at a given segment gives rise to abnormal loading and motion at adjacent segments, leading eventually to adjacent segment morbidity.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinous processes and provides an elastic restraint to the spreading apart of the spinous processes which occurs during flexion. Such devices and methods for their use are described in U.S. Patent Publication No. 2005/02161017A1, published on Sep. 29, 2005, and having common inventors with the present application.

As illustrated in FIG. 2, an implant 10 as described in the '017 application typically comprises an upper strap component 12 and a lower strap component 14 joined by a pair of compliance members 16. The upper strap 12 is shown disposed over the top of the spinous process SP4 of L4 while the lower strap 14 is shown extending across the bottom of the spinous process SP5 of L5. The compliance member 16 will typically include an internal element, such as elastomeric members 72a and 72b (FIG. 7 of the '017 application) which are attached to inelastic cables 76a and 76b in such a way that the cables may be "elastically" or "compliantly" pulled apart as the spinous processes SP4 and SP5 move apart during flexion. In particular, the compliance or elasticity is provided by the cables compressing the elastomeric members 72a and 72b between stoppers elements 78a, 78b, 80a, and 80b at their respective ends. In this way, the implant provides an elastic tension on the spinous processes which provides a force that resists flexion. The force increases as the processes move further apart and the rubber or elastomeric blocks become more compressed. Usually, the straps or cables themselves will be essentially non-compliant so that the degree of elasticity or compliance may be controlled and provided solely by the nature of the elastomeric members in compliance members 16.

While potentially robust over millions of cycles of use, the "compressive" compliance members of the '017 application can have difficulty in providing controlled elastic tension within the relatively low 25 N/mm to 75 N/mm range set forth in the application. The use of compressive rubber or elastomeric blocks in the compliance members also limits the length of device elongation which can be achieved. Even if the initial compression provided by the block is within the target elastic resistance range, the stiffness of the compressive block would be expected to rise quickly and potentially fall outside of the target range as the block is further compressed by pulling of the spinous processes on the upper and lower straps. Moreover, even such relatively "low" stiffnesses above 25N/mm can present some risk of damage or trauma to the spinous processes and other parts of the vertebrae and spine. In order to reduce the compressive force and increase the compressive length, the size of the compressive block may be increased. Increasing the size of the compressive block, however, increases the overall size of the device and is undesirable. The need to have the straps or cables traverse the entire length of the compressive block also increases the size and complexity of the implant structure. Increasing the size of the device is undesirable for many reasons, including making implantation more difficult, while increasing the complexity of the device is undesirable as it increases the risk of failure.

For these reasons, it would be desirable to provide improved spinal implants and methods for their use in inhibiting flexion in patients suffering from discogenic pain. It would be particularly desirable if the improved devices could reliably and repeatedly provide relatively low initial tension on the spinous processes and a relatively low elastic resistance to flexion, even over relatively long lengths of travel. Moreover, any risk of damage to the vertebrae of spine should be minimized. In addition, the devices should have a relatively small size with a decreased complexity in order to facilitate implantation and reduce the risk of failure. Furthermore, the devices should be designed to continue to function even after being cycled for long periods of time (e.g. up to multiple years of implantation) through high numbers of cycles (e.g. up to millions of cycles) and as such should exhibit primarily elastic behavior with minimal plasticity, i.e., low creep. At least some of these objectives will be met by the inventions described hereinbelow.

2. Description of the Background Art

US Patent Publication No. 2005/0216017A1 has been described above. US 2005/0192581 describes an orthopedic tether which can have a stiffness from at least 1N/mm to at least 200N/mm and which can be used for many purposes, including wrapping spinous processes. Other patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; US 2006/0069447; US 2006/0136060; US 2006/0240533; US 2007/0213829; US 2007/0233096; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1. The mechanical properties of flexible constraints applied to spinal segments are described in Papp et al. (1997) *Spine* 22:151-155; Dickman et al. (1997) *Spine* 22:596-604; and Garner et al. (2002) Eur. Spine J. S186-S191; A1 Baz et al. (1995) *Spine* 20, No. 11, 1241-1244; Heller, (1997) *Arch. Orthopedic and Trauma Surgery*, 117, No. 1-2:96-99; Leahy et al. (2000) *Proc. Inst. Mech. Eng.* Part H: *J. Eng. Med.* 214, No. 5: 489-495; Minns et al., (1997) *Spine* 22 No. 16:1819-1825; Miyasaka et al. (2000) *Spine* 25, No. 6: 732-737; Shepherd et al. (2000) *Spine* 25, No. 3: 319-323; Shepherd (2001) *Medical Eng. Phys.* 23, No. 2: 135-141; and Voydeville et al (1992) *Orthop Traumatol* 2:259-264.

SUMMARY OF THE INVENTION

The present invention provides spinal implants and methods for their use in restricting spinal flexion for the treatment of discogenic pain and other spinal conditions, such as spondylolisthesis, where the physician may desire to control spinal flexion. The implants and methods are particularly intended to dynamically limit flexion of at least one spinal segment by applying an elastic resistance between spinous processes on a pair of vertebrae, typically adjacent vertebrae, or between a spinous process, usually on L5, and a sacrum. The intent of the implants and methods is to limit motion between the vertebra while allowing at least several degrees of measurable motion. This will restrict flexion at the segment of interest without abnormally loading adjacent vertebral segments. It has been found by the inventors herein that by applying a very low elastic resistance to flexion of the spinal segment, typically below 25 N/mm, preferably below 20 N/mm, usually in the range from 7.5 N/mm to 20 N/mm, and preferably in the range from 10 N/mm to 15 N/mm, effective pain relief can be achieved with minimum risk of damage to the spinous processes and other vertebral and spinal structures which could result from restriction with relatively rigid structures and even elastic structures with higher elastic resistances.

The preferred methods and systems of the present invention will provide a minimum and preferably no elastic resistance to extension of the spinal segments. The preferred methods and systems of the present invention will usually be coupled to the spinous processes via flexible straps which, by virtue of their placement around the spinous processes and their flexible nature, make it very difficult for the preferred methods and systems of the present invention to provide any resistance to extension. Furthermore, the implants of the present invention will usually be free from structure located between adjacent spinous processes, although in some cases structure may be provided where the structure does not substantially interfere with or impede the convergence of the spinous processes as the spine undergoes extension. While some small amount of elastic resistance to extension might be found, it will preferably be below 3 N/mm, more preferably below 1 N/mm, and usually below 0.5 N/mm.

Similarly, the preferred methods and systems of the present invention will provide a minimum and preferably no elastic resistance to lateral bending or rotation of the spinal segments. The preferred methods and systems of the present invention will usually be coupled to the spinous processes via flexible straps which, by virtue of their placement around the spinous processes and their flexible nature, make it very difficult for the preferred methods and systems of the present invention to provide any resistance to lateral bending or rotation. This is particularly true in the lumbar spine where the range of motion in rotation is usually limited to ±3°. While some small amount of elastic resistance to lateral bending or rotation might be found, it will preferably be below 3 N/mm, more preferably below 1 N/mm, and usually below 0.5 N/mm.

As used herein, the phrase "spinal segment" refers to the smallest physiological motion unit of the spine which exhibits mechanical characteristics similar to those of the entire spine. The spinal segment, also referred to as a "functional spinal unit" (FSU), consists of two adjacent vertebrae, the intervertebral disk, and all adjoining ligaments and tissues between them. For a more complete description of the spinal segment or FSU, see White and Panjabi, *Clinical Biomechanics of the Spine*, J. B. Lippincott, Philadelphia, 1990.

As used herein, "neutral position" refers to the position in which the patient's spine rests in a relaxed standing position. The "neutral position" will vary from patient to patient. Usually, such a neutral position will be characterized by a slight curvature or lordosis of the spine where the spine has a slight anterior convexity and slight posterior concavity. In some cases, the presence of the constraint of the present invention may modify the neutral position, e.g. the device may apply an initial force which defines a new neutral position having some small extension of the untreated spine. As such, the use of the term "neutral position" is to be taken in context of the presence or absence of the device. As used herein, "neutral position of the spinal segment" refers to the position of a spinal segment when the spine is in the neutral position.

As used herein, "segmental flexion" refers to the motion between adjacent vertebrae in a spinal segment as the patient bends forward. Referring to FIG. 1A, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Segmental flexion thus refers to the relative movement between adjacent vertebrae as the patient bends forward from the neutral position illustrated in FIG. 1A.

As used herein, "segmental extension" refers to the motion of the individual vertebrae L as the patient bends backward and the spine extends from the neutral position illustrated in FIG. 1A. As the patient bends backward, the anterior ends of the individual vertebrae will move apart. The individual spinous processes SP on adjacent vertebrae will move closer together in a direction opposite to that indicated by arrow B.

As used herein, the phrase "elastic resistance" refers to an application of constraining force to resist motion between successive, usually adjacent, spinous processes such that increased motion of the spinous processes results in a greater constraining force. The elastic resistance will, in the inventions described herein, inhibit motion of individual spinal segments by, upon deformation, generating a constraining force transmitted directly to the spinous processes or to one or more spinous process and the sacrum. The elastic resistance can be described in units of stiffness, usually in units of force per deflection such as Newtons per millimeter (N/mm). In some cases, the elastic resistance will generally be constant (within ±5%) over the expected range of motion of the spinous processes or spinous process and sacrum. In other cases, typically with elastomeric components as discussed below, the elastic resistance may be non-linear, potentially varying from 33% to 100% of the initial resistance over the physiologic range of motion. Usually, in the inventions described herein, the pre-operative range of motion of the spinous process spreading from the neutral or upright position to a maximum flexion-bending position will be in the range from 2 mm to 20 mm, typically from 4 mm to 12 mm. With the device implanted, the post-operative range of motion of the spinous process spreading from the neutral or upright position to a maximum flexion-bending position will be reduced and will usually be in the range from 1 mm to 10 mm, typically from 2 mm to 5 mm. Such spinous process spreading causes the device to undergo deformations of similar magnitude.

In a first specific aspect of the present invention, a method for restricting flexion of at least one spinal segment comprises implanting a constraining structure having a superior end coupled to a superior spinous process and an inferior end coupled to an inferior spinous process or a part of the sacrum. The constraining structure provides an elastic resistance to flexion beyond a neutral position of the spinal segment in the ranges set forth above. Preferably, the constraining structure provides substantially no resistance to extension of the spinal segment beyond the neutral position, typically being below the forces set forth above. The constraining structure may be implanted by placing a superior tether structure over or through the superior spinous process and placing an inferior tether structure over or through the inferior spinous process or part of the sacrum. The tether structures are preferably non-distensible and joined by at least one compliance member which provides the desired elastic resistance to flexion. In the exemplary embodiments, the superior and inferior tether structures will be joined by a pair of compliance members which are symmetrically placed on the right and left sides of a midline of the spinal segment, where each compliance member provides about one half of the total elastic resistance to be applied to the spinal segment. That is, the individual compliance members will preferably provide an elastic resistance below 12.5 N/mm, usually below 10 N/mm, typically in the range from 3.75 N/mm to 8.75 N/mm, and preferably in the range from 5 N/mm to 7.5 N/mm.

The elastic resistance to flexion applied by the constraining structure of the present invention is exerted when the spinal segment moves beyond the neutral position and will depend on several factors including the elastic characteristics of the constraining structure, the position of the constraining structure on the spinous processes, the dimensions of the constraining structure, and the patient's anatomy and movement. The constraining structure will usually be positioned so that the upper and lower tethers engage the middle anterior region of the spinous process, and the dimensions of the constraining structure will usually be adjusted so that the tethers are taut, i.e. free from slack, but essentially free from tension (axial load) when the spinal segment is in its neutral position, i.e., free from flexion and extension. As the segment flexes beyond the neutral position, the constraining structure will immediately provide an elastic resistance in the ranges set forth above.

In some cases, the dimensions and assembly of the construct will be selected so that the tethers and compliance members are slightly pre-tensioned even before the compliance members are under load. Thus, the constraining structure will apply a predetermined resistive force, typically in the range from 5N to 25N, as soon as the spinal segment flexes from the neutral position. In the absence of such pre-tensioning, the compliance members would apply a zero resistive force at the instant they are placed under load. In all cases, as the segment flexes beyond the treated neutral position, the constraining structure will provide increasing elastic resistance in the ranges set forth above.

Usually, the constraining structures will apply minimal or no force when the spinal segment is in the neutral position. In some instances, however, it may be desirable to tighten the constraining structure over the spinous processes so that a relatively low finite force (typically in the range from 1N to 25N, usually from 5N to 15N) is applied even before flexion while the spinal segment remains at a neutral position.

The relatively low elastic resistance afforded by the constraining structures of the present invention is advantageous because the resulting low forces allow the constraining structure to resist flexion sufficiently to improve the underlying pain or instability with a reduced risk of injury from excessive force. In particular, the preferred elastic resistance ranges set forth above provide sufficient constraint to effect a significant change in flexion in the typical patient while allowing a significant safety margin to avoid the risk of injury. The elastic resistance provided by the constraints of the present invention will limit the separation of the spinous processes on the treated spinal segment which is desirable both to reduce flexion-related pain and spinal instability.

The resistance to flexion provided by the elastic constraints of the present invention will reduce the angular range-of-motion (ROM) relative to the angular ROM in the absence of constraint. Angular ROM is the change in angle between the inferior end plate of the superior vertebral body of the treated segment and the superior endplate of the inferior vertebral body of the treated segment when the segment undergoes flexion. Thus, the treatments afforded by the elastic constraints of the present invention will provide a relatively low angular ROM for the treated segment, but typically a ROM higher than that of a fused segment.

While the constraint structures of the present invention will limit flexion, it is equally important to note that in contrast to spinal fusion and immobilizing spinal spacers, the methods and devices of the present invention will allow a controlled degree of flexion to take place. Typically, the methods and devices of the present invention will allow a degree of flexion which is equal to at least about 25% of the flexion that would be observed in the absence of constraint, more typically being at least about 50%. By reducing but not eliminating flexion, problems associated with fusion, such as increased pain, vertebral degeneration, instability at adjacent segments, and the like, may be overcome.

In some instances, the constraint structures of the present invention will act to restore the stiffness of a spinal segment which is "lax" relative to adjacent segments. Often a patient with flexion-related pain or instability suffers from a particular looseness or laxity at the painful segment. When the patient bends forward or sits down, the painful, lax segment will preferentially flex relative to the stiffer adjacent segments. By adjusting the devices of the present invention so that they are taut when the spinal segment is in its neutral position, the stiffness of the treated segment can be "normalized" immediately as the patient begins to impart flexion to the spine. Thus, premature and/or excessive flexion of the target spinal segment can be inhibited or eliminated.

The protocols and apparatus of the present invention allow for individualization of treatment. Compliance members with different stiffnesses, elongations (lengths of travel), and other characteristics can be selected for particular patients based on their condition. For example, patients suffering from a severe loss of stiffness in the target spinal segment(s) may be treated with devices that provide more elastic resistance. Conversely, patients with only a minimal loss of natural segmental stiffness can be treated with devices that provide less elastic resistance. Similarly, bigger patients may benefit from compliance members having a greater maximum elongation, while smaller patients may benefit from compliance members having a shorter maximum elongation.

For some patients, particularly those having spinal segments which are very lax, having lost most or all of their natural segmental stiffness, the present invention can provide for "pre-tensioning" of the constraining structure. As described above, one way to accomplish this is by shortening the constraining structure such that a small amount of tension is held by the constraining structure when the spine is in the neutral or slightly extended initial position. Alternatively, pre-tensioned compliance elements can be provided to pre-tension the constraining structure without changing its length. The tension or compression elements utilized in the compliance members of the present invention, such as coil springs, elastomeric bodies, and the like, will typically present little or no elastic resistance when they are first deformed. Thus, there will be some degree of elongation of the compliance members prior to the spinal segment receiving a therapeutic resistance. To provide a more immediate relief, the tension or compression members may be pre-tensioned to have an initial static resistive force which must be overcome to initiate deformation. In this way, a constrained spinal segment will not begin to flex at the instant the patient begins to flex her or his spine which is an advantage when treating lax spinal segments. Certain specific embodiments for achieving such pre-tensioning are described in detail below.

In a second specific aspect of the present invention, a device for restricting flexion of at least one spinal segment comprises a constraint adapted to couple to at least one superior spinous process and at least one inferior spinous process. The constraint has at least one dimension that is adjustable to allow tightening over the spinous processes or spinous process and sacrum intra-operatively. The constraint will also provide a resistance to flexion of the spinal segment beyond the neutral position in the ranges set forth above. Preferably, the constraint provides little or no elastic resistance to extension beyond the neutral position within the limits set forth above. Usually, the constraint comprises a superior tether structure adapted to couple to the superior spinous process and an inferior tether structure adapted to couple to the inferior spinous process or sacrum. The tether structures may be a single, continuous segment, such as a band, cable, cord, strap, braid, webbing, or the like. Alternatively, the tether structure may comprise two or more individual components attached in a series, in parallel, or in any other configurations. Typically, the tether structures will be non-compliant so that they are essentially non-extensible when subjected to an axial force, typically elongating less than 5%, usually elongating less than 2% when subjected to a force of 100 N; in the context of the application of such tether structures across a pair of spinous processes or a spinous process and sacrum, such elongations will typically by less than 2 mm, usually less than 1 mm. Preferably, the devices of the present invention will comprise at least two compliance members arranged to lie symmetrically on either side of a midline of the spinal segment when the tether structures are placed over the spinous processes or spinous process and sacrum.

Because the constraining structures of the present invention will be implanted for a number of years, often over millions of use cycles, it is desirable that the elastic constraints of the present invention remain dimensionally constant and have constant elastic characteristics. By combining the discrete compliance members with non-compliant tethers or straps, the dimensional stability of the devices will be improved, particularly relative to other constraining structures which employ elongate polymeric cables for constraining adjacent spinous processes. In a preferred embodiment of the present invention, the tethers joining the compliance members will be non-distensible and have a very high tensile strength, preferably greater than 500N, more preferably greater than 2000N. Such a high tensile strength will minimize "creep" (elongation over time) in the tether structures, preferably so that the long-term creep of the tethers under physiologic loads will be less than 10%, usually less than 5% and preferably less than 1%, over millions of use cycles and many years so that overall elongation of the constraint contributed by the tethers over the implanted life of the constraint will be less than 2 mm, usually less than 1 mm, and preferably less than 0.5 mm. The use of woven tethers, such as woven polymeric tethers, is strictly advantageous for their flexibility in non-loaded directions, and since the fibers are oriented in a direction which is aligned with that of the load. Moreover, by limiting elastic elongation to the compliance members, the dimensional stability can be improved by appropriate selection of materials and design.

In a third specific aspect of the present invention, a system for restricting flexion of at least one spinal segment comprises a superior tether structure, an inferior tether structure, a right compliance member, and a left compliance member. The superior tether structure is adapted to couple to a superior spinous process and includes a right connecting segment and a left connecting segment. Usually, the tether structure will be very flexible but essentially non-extensible so that it will stretch very little when subjected to the axial loads experienced after it is implanted. The particular limits on extensibility are described above. The inferior tether structure will have similar properties and is adapted to couple to the inferior spinous process or to a sacrum. The right compliance member includes a tension element having an upper end connectable to the right connecting segment of the superior tether structure and a lower end connectable to the right connecting segment of the inferior tether structure. The left compliance member includes a tension element having an upper end connectable to the left connecting segment of the superior tether structure and a lower end connectable to the left connecting element of the inferior tether structure. Thus, the systems for restricting flexion may be implanted symmetrically over a pair of successive or adjacent spinous processes or over a spinous process of a lower vertebra, typically L5, and the sacrum. Usually the tether structures will be connected to the tension members near a center of the compliance member to minimize off-access loading. In other embodiments, however, the connections may be made off-center.

For ease of implantation, one connecting segment of each of the tether structures is usually pre-attached to one end of the tension element of each of the two compliance members. Usually, the pre-attached end will be fixedly attached. The other, free end of each tether structure will usually be received in an adjustable connecting element or component which is part of the other compliance member, as described in more detail below. The adjustable connecting element will preferably be reversibly adjustable, allowing positioning and repositioning of the tether relative to the compliance member without damaging either component. A particularly preferred example of such an adjustment member is a roller which is described in detail hereinafter. Optionally, the compliance members may comprise a sheath which covers the tension element. Optionally, the sheath may incorporate battens which prevent the sheath from interacting with the coils (e.g. by pinching or wearing). Further optionally, the compliance members may each comprise an element that limits elongation, such as a cord or the like. Usually, such elongation limit prevents elongation of the tension element to 20 mm, preferably to 10 mm beyond its neutral unstressed condition.

In a particular embodiment of the systems of the present invention, the tension elements each comprise a coil spring having a superior tether connector and an inferior tether connector. One of the tether connectors on each tension element will be adapted for fixed attachment while the other will be adapted for adjustable attachment. Usually, the coil spring and tether connectors are formed from a single piece of material, such as a metal blank or rod. Alternatively, they may be formed from a single polymeric blank. The adjustable connector may comprise a rotatable roller for adjustably receiving a connecting segment of the free tether structure from the other compliance member. In a second particular embodiment of the systems of the present invention, the tension elements comprise an elastomeric body having a superior tether connector and an inferior tether connector. The elastomeric body typically comprises a beam having discrete superior and inferior passages to define the tether connectors. Alternatively, the elastomeric body may comprise a ring having a central opening which defines both the tether connectors. The elastomeric body comprises an elastomer having a relatively low durometer, such as silicone rubber as well as various thermoplastics and thermosetting elastomers. In a preferred aspect, the elastomeric body may be pre-cycled and tensioned to stabilize the stiffness value. The stiffness value will typically be in the ranges set forth above.

BRIEF DESCRIPTION OF THE DRAWINGS

FIGS. 7A-7C illustrate a second exemplary tension element suitable for incorporation in a compliance member in accordance with the principles of the present invention. In this embodiment, the tension element comprises an elastomeric body having superior and inferior passages which define tether connectors.

FIGS. 8A-8C illustrate a third exemplary tension element suitable for incorporation in a compliance member in accordance with the principles of the present invention. In this embodiment, the tension member comprises a ring having a single central opening which defines superior and inferior tether connectors.

FIGS. 8D-8G illustrate a fourth exemplary tension element suitable for incorporation in a compliance member in accordance with the principles of the present invention. In this embodiment, the tension member comprises an elastomeric body having upper and lower cap members for attachment to superior and inferior tether connectors.

FIGS. 9A-9B illustrate a fifth exemplary tension element suitable for use as a compliance member in accordance with the principles of the present invention. In this embodiment, the tension element comprises an S-shaped spring having integral superior and inferior tether structure connectors.

FIGS. 14A and 14B illustrate tension and compression members having pre-tensioned tension elements.

FIGS. 15A and 15B are force-displacement graphs which illustrate the difference between the pre-tensioned and non-pre-tensioned tension and compression members.

DETAILED DESCRIPTION OF THE INVENTION

Figure 1:
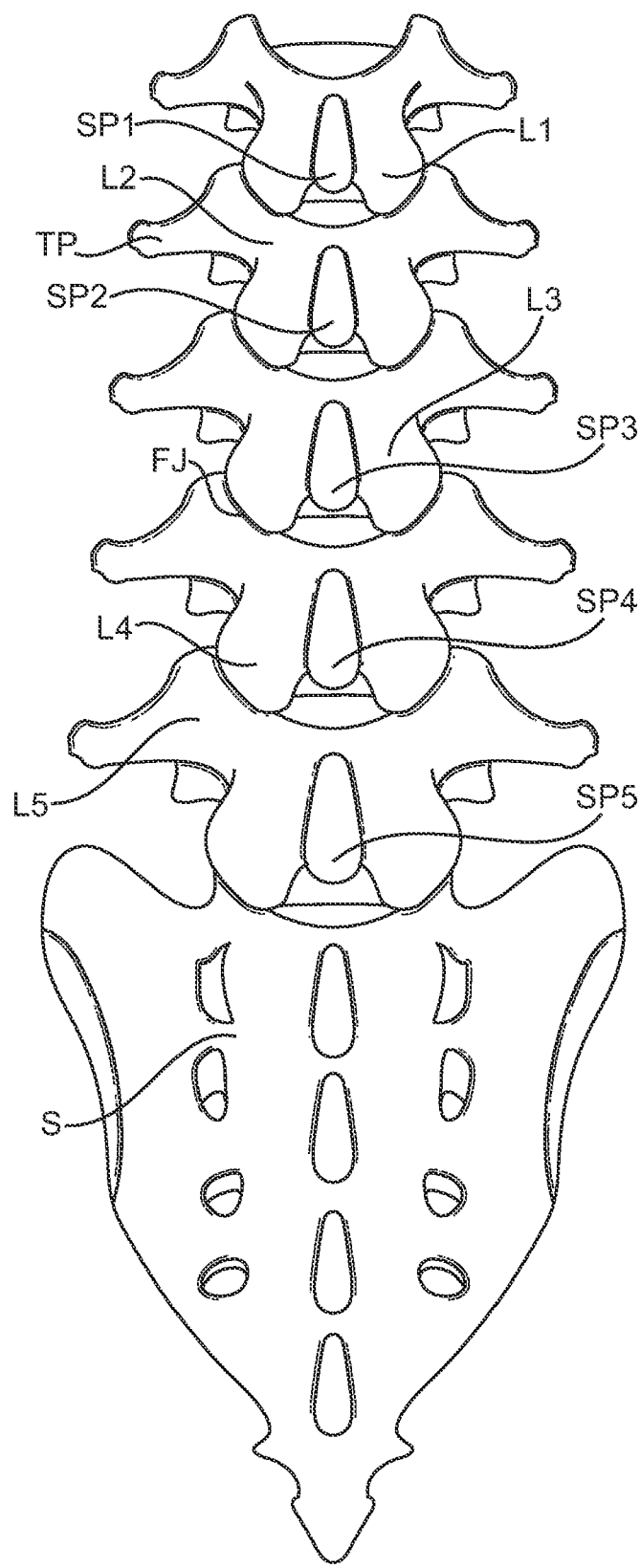
FIG. 1 is a schematic diagram illustrating the lumbar region of the spine including the spinous processes (SP), facet joints (FJ), lamina (L), transverse processes (TP), and sacrum (S).
Figure 1A:
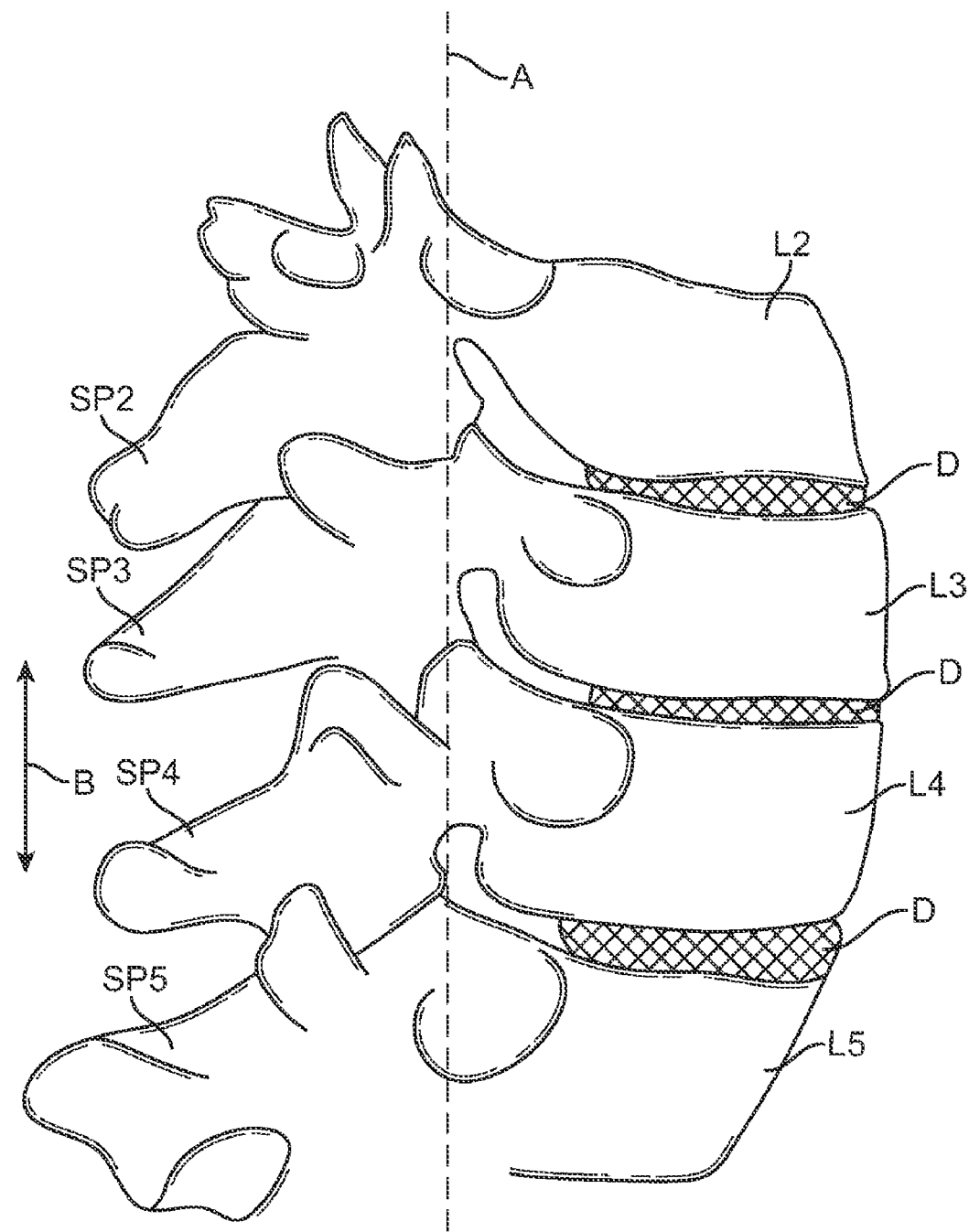
FIG. 1A is a schematic illustration illustrating a portion of the lumbar region of the spine taken along a saggital plane.
Figure 2:
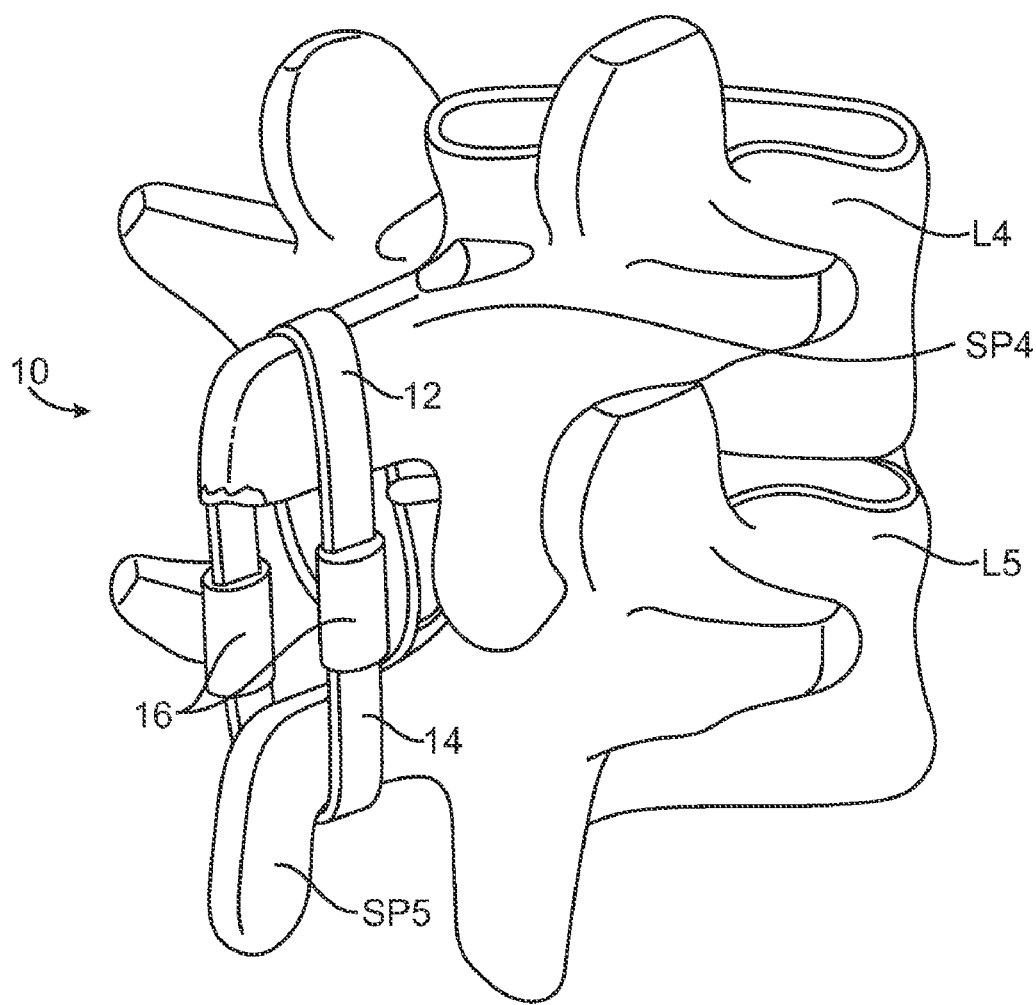
FIG. 2 illustrates a spinal implant of the type described in US 2005/0216017A1.
Figure 3:
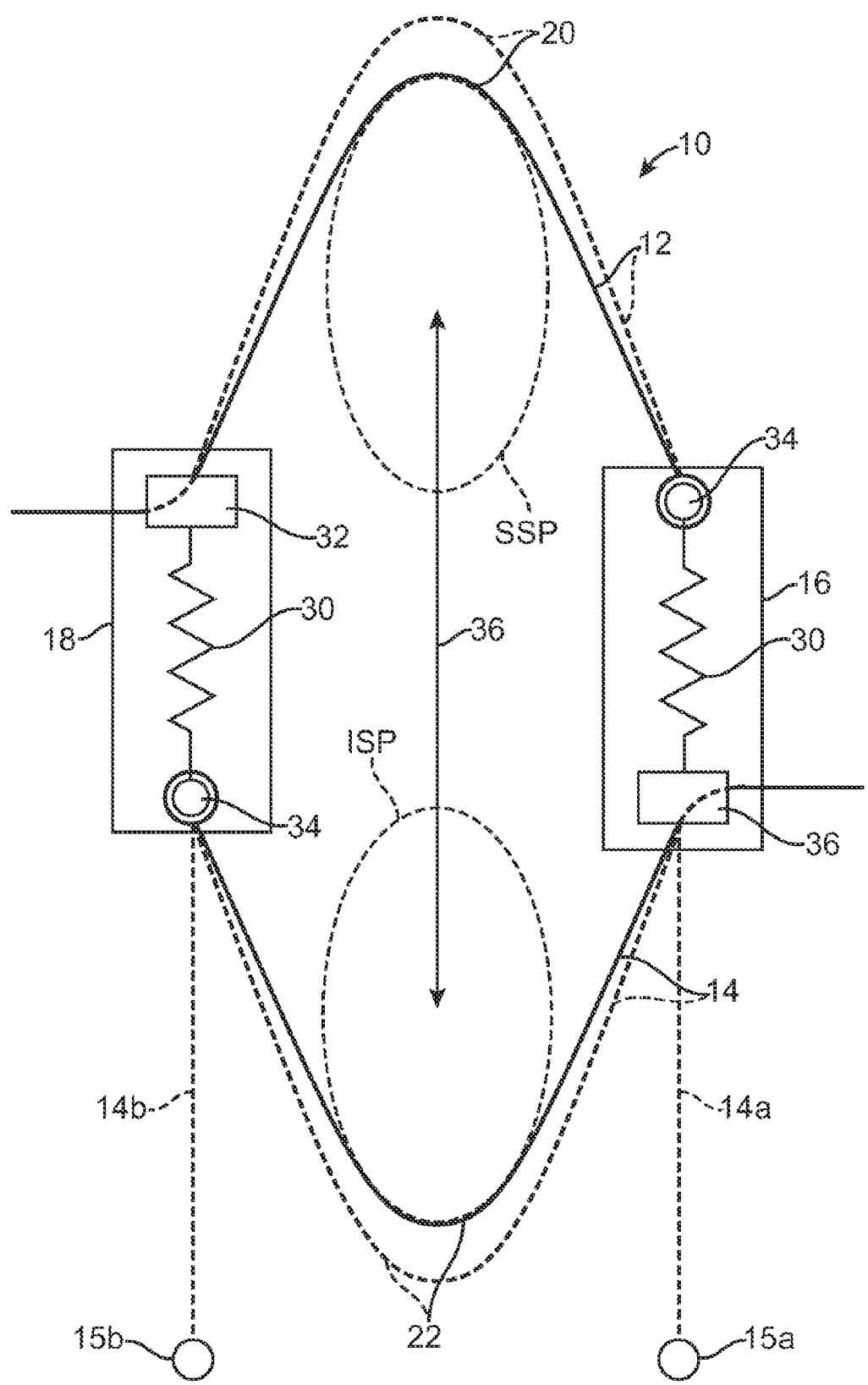
FIG. 3 is a schematic illustration of the systems of the present invention comprising superior and inferior tether structures and right and left compliance members.

Exemplary spinous process constraints according to the present invention are illustrated schematically in FIG. 3. The systems 10 comprise a superior tether structure 12, and inferior tether structure 14, and right compliance member 16 and a left compliance member 18. The superior tether structure 12 will typically be a continuous band, cable, strap, cord, or other structure which extends between the two compliance members and provides a saddle region 20 which is adapted to lie over and conform to a superior surface of a superior spinous process SSP as described in more detail in the related prior applications which have been incorporated herein by reference. The inferior tether structure 14 will typically comprise a band, cable, or the like which is constructed similarly if not identically to the superior tether structure 12 and has a saddle region 22 adapted to lie over and conform to an inferior surface of an inferior spinous process 22. In certain instances, however, the inferior tether structure 14 may comprise separate bands, cables, straps, cords, or the like, 14a and 14b, shown in broken line, which have anchors 15a and 15b at their lower ends and are adapted to be separately attached to an inferior vertebrae or more commonly to a sacrum. The use of such separate tether structures for inferior attachment are described in more detail in co-pending application Ser. No. 11/827,980, the full disclosure of which has been previously incorporated herein by reference. The tether structures will usually be flexible but effectively non-compliant so that they allow minimum elongation under tensile load.

The right and left compliance members 16 and 18 will usually have similar or identical constructions and include an adjustable attachment component 32 and a fixed attachment component 34 for securing connecting segments of the superior and inferior tether structures 12 and 14. Usually, each compliance member 16 and 18 will have one of the tether structures 12 and 14 pre-attached to the fixed attachment component 34. The two subassemblies can then be introduced onto opposite sides of the spinous processes, and the tether structures placed over the spinous processes or otherwise attached to the vertebral bodies, as generally described in co-pending application Ser. No. 11/875,674, the full disclosure of which is incorporated herein by reference.

The present invention is particularly concerned with the nature of the tension elements 30, and a number of specific embodiments will be described hereinbelow. In general, the tension elements 30 will elastically elongate as tension is applied by the superior and inferior tether structures 12 and 14 through the attachments 32 and 34, in the direction shown by arrow 36. As the spinous processes or spinous process and sacrum move apart during flexion of the constrained spinal segment, the superior and inferior tether structures 12 and 14 will also move apart, as shown generally in broken line in FIG. 3. A tension element 30 will elastically resist the spreading with a force determined by the mechanical properties of the tension member. In particular, the tension members will be selected to have a tensile or elastic stiffness, also known as a spring constant, in the relatively low ranges set forth above. Such low elastic constricting forces provide a number of advantages when compared to complete restriction or constriction with a high elastic force as described above.

Figure 4:
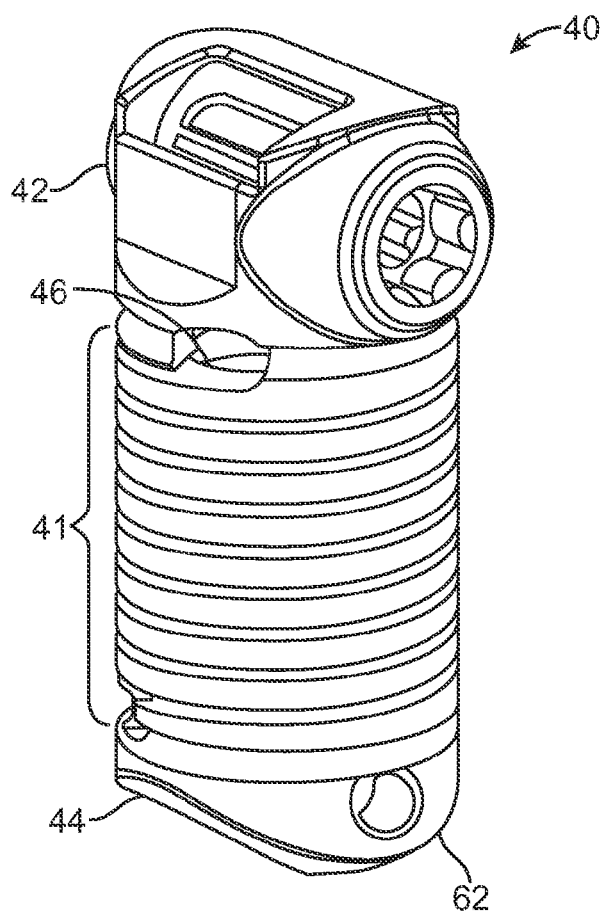
FIG. 4 illustrates an exemplary coil spring tension member.
Figures 5A, 5B:
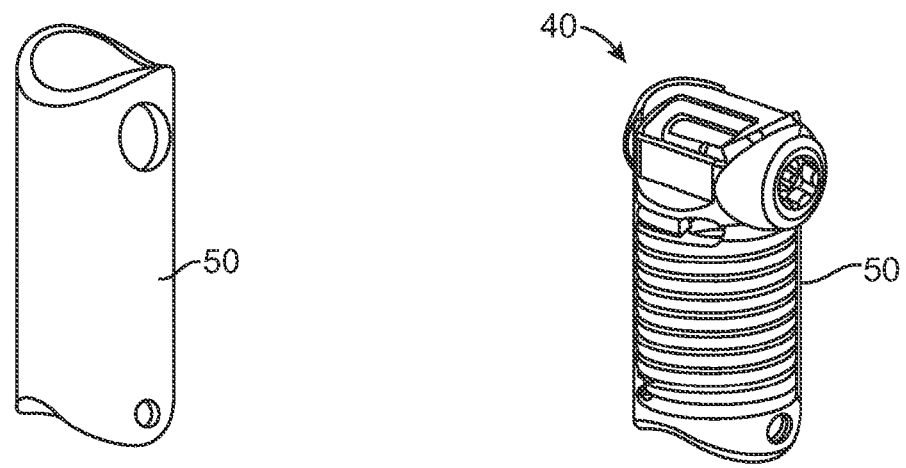
FIGS. 5A and 5B illustrate a sheath and placement of the sheath over the coil spring tension member of FIG. 4.

A first exemplary tension element 40 constructed in accordance with the principles of the present invention is illustrated in FIGS. 4, 5A and 5B. The tension element 40 comprises a helical spring structure 41 formed from a single piece of material. The tension member 40 includes an adjustable tether connector 42 and a fixed tether connector 44, both of which are preferably formed integrally or monolithically with the helical spring structure 41. Typically, the helical spring structure 41 and both tether connectors 42 and 44 will be formed from one piece of material, usually being a metal such as titanium, but optionally being a polymer, ceramic, reinforced glass or other composite, or other material having desired elastic and mechanical properties and capable of being formed into the desired geometry. In a preferred embodiment, the tension member 40 is machined or laser cut from a titanium rod. Alternatively, a suitable polymeric material will be polyethylene ether ketone (PEEK). Other features may be built into the tension member 40, such as a stress relief hole 46. Components that mate with the adjustable tether connector may potentially include a roller and a lock-nut; such components could be made from the same material as the tension element and adjustable tether connector (e.g. titanium components if the tension member is titanium), or they could be made from a different material (e.g. injection molded PEEK).

The exterior of the tension member 40 may be covered with a protective cover, such as the elastomeric sheath 50 illustrated in FIG. 5A. The sheath 50 may be placed over the body of the tension member 40, as illustrated in FIG. 5B, in order to prevent the intrusion of tissue and body materials into the spaces between the turns of the coil and interior of the element.

Figure 6A:
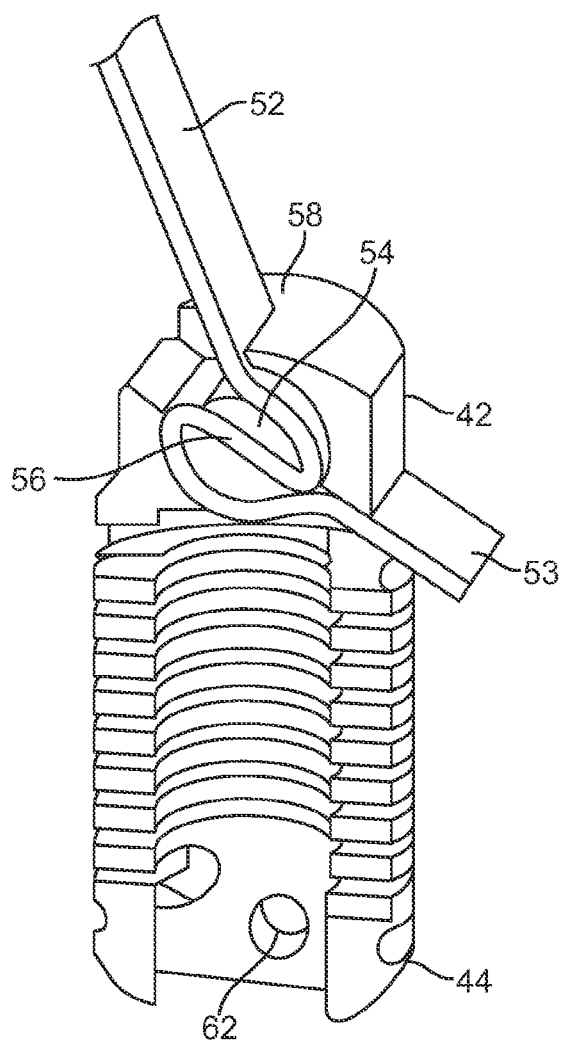
FIGS. 6A-6C illustrate the use of a locking mechanism incorporated in the tension member of FIG. 4 for removably securing a band member of a tether structure.
Figure 6B:
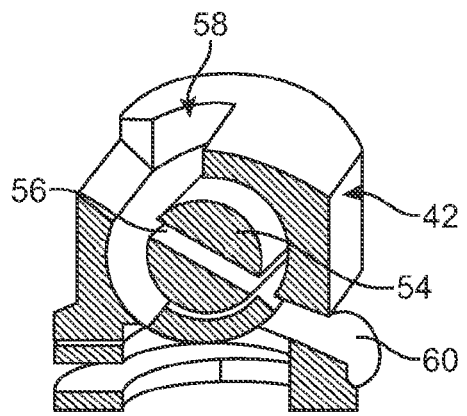
Figure 6C:
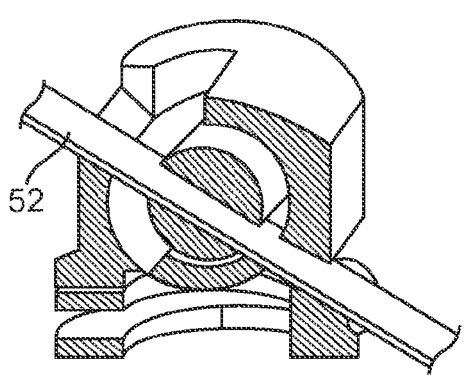

A free end 53 of the tether structure 52 may be attached to the adjustable tether connector 42, as illustrated in FIG. 6A through 6C. Initially, a barrel locking mechanism 54 is rotationally aligned such that a slot 56 is aligned with an inlet opening 58 on the top of the connector 42 and an outlet opening 60 on the side of the connector. The inlet opening 58 is located centrally and providing a primarily axial load on the compliance member, thereby evenly loading the compliance member and having the advantages described above. The free end 55 of tether 52 is then advanced through the inlet opening 58, slot 56, and outlet opening 60, as illustrated in FIG. 6C. By then rotating the barrel lock 54 90° to 180°, the tether 52 will be locked in place in the connector 42, as shown in FIG. 6A. It will be appreciated that this simple locking mechanism allows tether 52 to be appropriately tensioned for the individual patient before locking the tether in place. A locking feature, e.g. set screw, nut, or pin (not shown) would then be used to lock the tether and roller in place, providing additional resistance to unfurling and opening. The tensioning could be performed separately and/or simultaneously during implantation of the constraint assembly. Additional features of the mechanism such as pins, shoulders, or other features which control the travel of the roller or lock-nut may aid in the alignment and operation of the mechanism.

Another tether structure (not illustrated) will be attached to the fixed connector 44 at the other end of the tension element 40, typically using a pin (not illustrated). The pin may be anchored in a pair of receiving holes 62, and a free end of the tether wrapped over the pin and firmly attached. Usually, the fixed tether structure will be pre-attached at the time of manufacture so that the treating physician can implant each of the pair of tension members, with one tether structure attached to the fixed tether connector. The remaining free ends of each tether structure 52 may then be deployed around the spinous processes (or attached to a sacrum) in a pattern generally as shown in FIG. 3.

An alternative tension element 66 comprising an elastomeric body 68 is illustrated in FIGS. 7A-7C. The elastomeric body 68 comprises a central tensile segment 70 joined by a pair of ring connectors 72 and 74. The entire structure will be molded or cast from an elastomeric material having mechanical properties that provide the desired elastic stiffness or spring force, as set forth above. A particularly suitable elastomer is silicone rubber, but other thermoplastics and thermosetting elastomers could also be used.

The tension elements 66 may be joined to tether structures 76 and 78, as shown in FIG. 7B. As with the prior embodiments, each tether structure 76 and 78 is fixably attached to one tension element 66 at one end and adjustably attached to the other tension element at the other end. In particular, one end of the superior tether structure 76 is fixedly attached to the upper end of the left tension member 66 by wrapping around a shackle 80 which is attached to the ring connector 72 with a pin or bolt 82. Similarly, one end of the inferior tether structure 78 is fixedly attached to ring connector 72 on the lower end of the right tension element 66 using a shackle 82.

In contrast, adjustable attachment of the tether structures 76 and 78 is provided by a cord 84 which may be loosened or tightened in a locking structure comprising mating surfaces on a nut 86 and pin 88 assembly, as shown in FIG. 7C. The pin 88 is received in the ring connector 74 and holds a threaded cup 90 in place. The nut 86 is threadably received in the cup 90 and can be axially translated relative to the mating surface of pin 88. Thus, the cord 84 may be passed freely through the assembly when the nut 86 is loosened. Once the desired tension is placed on the tether structure 76 or 78, the nut 86 can be tightened to hold the cord 84 in place.

A further alternative embodiment of a tension element 100 is illustrated in FIGS. 8A-8C. The tension element 100 comprises a single elastomeric ring structure 102 having a large central opening 104. The elastomeric ring can be formed from any of the elastomers listed above for element 66. A pair of the tension elements 100 may be held in place by tether structures 106, as illustrated in FIG. 8B. Ends of the tether structures 106 may be looped through the central opening 104 to provide a continuous circumferential structure. As illustrated in FIG. 8B, there is no adjustability of the circumferential length of the structure. It will be appreciated, however, that at least one of the tether ends may be left free so that the loop may be tightened and then held in place, for example using crimping structure 110, as illustrated in FIG. 8C. Alternatively, four tether structures could be used, each pre-attached in the form of a permanent, closed loop around each end of each ring. Two inferior structures could then be attached (e.g. by crimping) to each other, and two superior structures could similarly be attached to each other.

Referring now to FIGS. 8D-8G, an alternative elastomeric tension element 200 comprises an elongate elastomeric body 202 having an upper cap member 204 and a lower cap member 206. The body 202 is formed from any of the elastomeric materials listed above and will provide an elastic resistance to elongation when opposite tensile forces are placed on the caps 204 and 206.

The elastomeric tension elements 200 may be incorporated into a superior tether structure 210 and an inferior tether structure 212, as seen in FIGS. 8E and 8F. Each of the tether structures 210 and 212 comprises a sheath 214 which is formed from a braided polymer or other substantially non-distensible fabric, textile or other material, typically being formed from polyester or polyethylene. The sheath has a generally tubular structure, and the braided or other fabric structure allows it to be radially expanded to accommodate an elastic tension element 200 at one end. As best seen in FIG. 8G, the elastic tension element 200 is placed in an end of the sheath 214 and secured by rings or bands 220 which are placed over the exterior of the sheath and which are held in place by collars 222. The collars 222 are typically formed from biologically inert polymer or metal, such as PEEK or titanium, and serve to transfer load from the sheath 214 to the cap members 204 and 206 and thus the elastomeric body 202 as a tensile load is placed on the sheath 214.

While the superior and inferior tether structures 210 and 212 could be joined in a variety of ways, a particularly convenient approach is to form a connecting loop 230 at the end of the sheath 214 which holds the elastic tensioning element 200. The loop 230 may be formed simply by stretching and folding the end of the sheath and attaching the end to the body of the sheath, by heat sealing, adhesives, crimps, or the like. After the loop is formed, the two tether structures 210 and 212 may be joined into a continuous loop for placement over the spinous processes by drawing distal ends 232 of each sheath 214 through the loop 230 of the opposite tether structure, as best seen in FIG. 8F. Once the proper tension is applied to the tether structures 210 and 212 by pulling on the distal ends, the distal end may be fixed in place, typically using an anchor 234 which can be crimped in place. Preferably but not necessarily, a slack region 240 will be provided in the sheath 214 between the retention rings 220 to allow desired elongation of the elastomeric body 202.

Figure 8H:
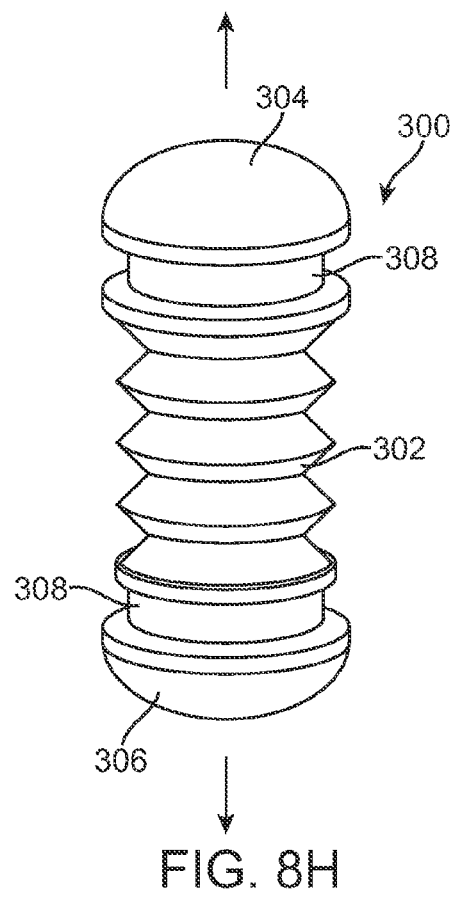
FIGS. 8H and 8I illustrate alternative embodiments for elastomeric tension elements suitable for incorporation into both tension and compression compliance members.
Figure 8I:
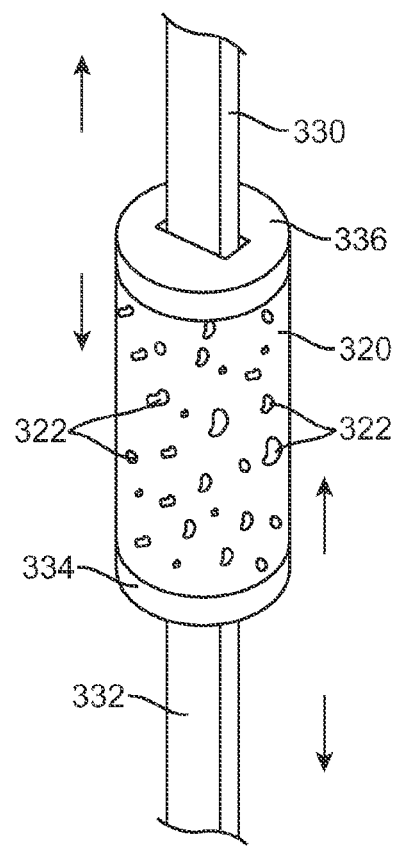

FIGS. 8H and 8I illustrate particular embodiments for elastomeric tension and compression elements suitable for use in the spinous process constraint systems of the present invention. In FIG. 8H the elastomeric tension element 300 is formed similarly to tension element 200 and includes an elastomeric body 302 having an upper cap member 304 and a lower cap member 306. The tension member 300 will typically also include collars 308 which are used to couple the tension member to tether structures. In order to enhance and control the elasticity or spring constant of the elastomeric body 302, the body is formed with a corrugated or "accordion" profile. The accordion profile allows the degree of elasticity to be increased relative to a similar sized elastomeric body having a cylindrical profile.

An elastomeric compression member 320 is illustrated in FIG. 8I. The elastomeric compression member 320 may be formed from any of the elastomeric materials described above, but will be formed to have a number of holes or voids 322. The formation of elastomers having such holes or voids may be accomplished by molding or extruding the elastomer with materials that are later removed to leave the voids in place. The presence of such voids in the elastomeric body 320 serves to enhance or help control the compressive elasticity of the member. Typically, the superior and inferior tether members 330 and 332 will pass through the body and be anchored on opposite ends to end caps 334 and 336, respectively, so that axial tension on the tether structures, as indicated by the outward arrows, will compress the elastomeric body 320, as indicated by the inwardly facing arrows.

Another flexion restriction system 120, as illustrated in FIGS. 9A-9B, comprises a pair of leaf spring structures 122, each of which includes an S-shaped center portion 122 and two tether connectors 126. Superior and inferior tether structures 130 and 132 respectively, each have two free ends which are adjustably received in the tether connectors 126. Each of the tether connectors 126 includes a screw with clamping surfaces 132 which may be loosened or tightened in order to permit adjustment of the tension on the tether structure as desired, as shown in FIG. 9B. The S-shaped center portion 124 of the leaf spring structure 122 may be formed from a metal, polymer, reinforced composite, or any other material which can be fabricated to provide an elastic stiffness or spring constant within the ranges described above. The tether connectors 126 may be formed integrally or monolithically with the center portions 124, or alternatively may be formed separately and adhered using adhesives, fasteners, or the like.

Figure 10A:
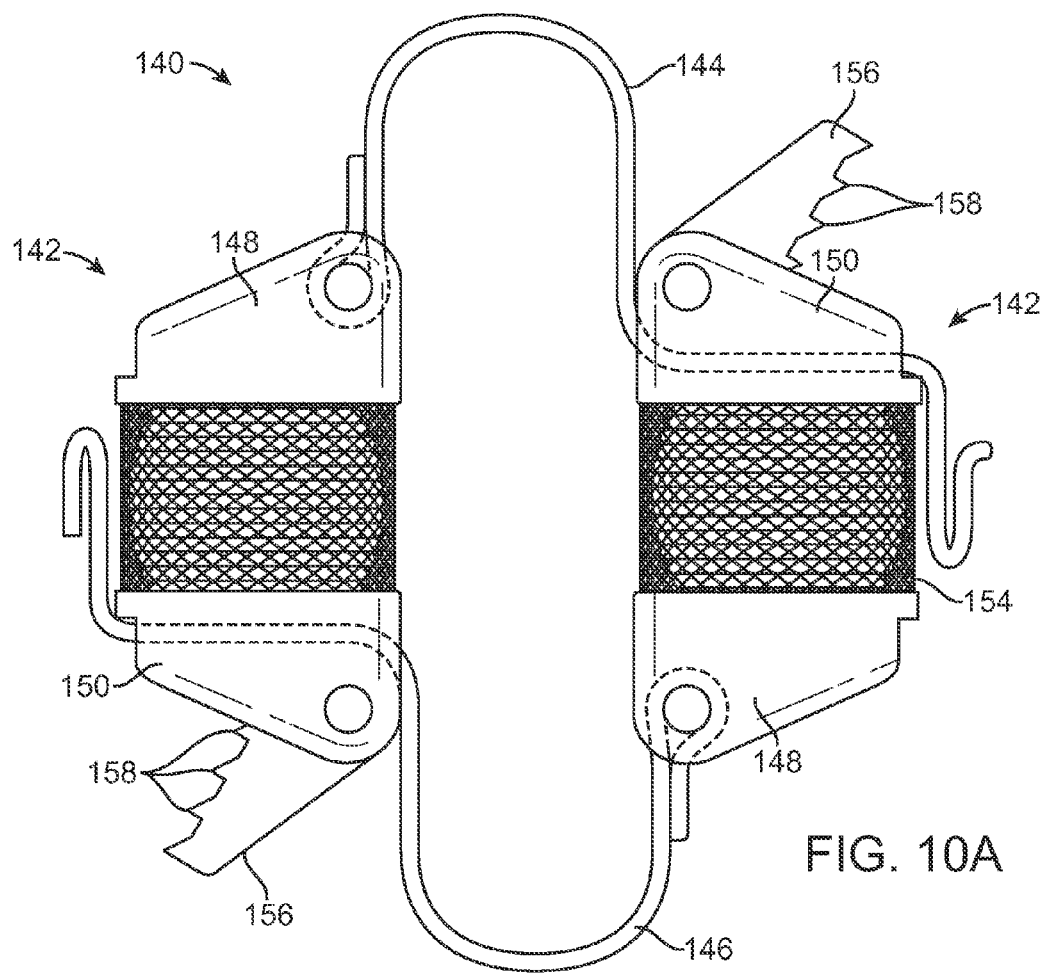
FIGS. 10A and 10B illustrate a sixth exemplary tension element which is used as part of a compliance member in accordance with the principles of the present invention. In this embodiment, the tension element comprises a helical spring having a lever arm or cam-locking tether connector and including a braided sheath for protecting the spring.
Figure 10B:
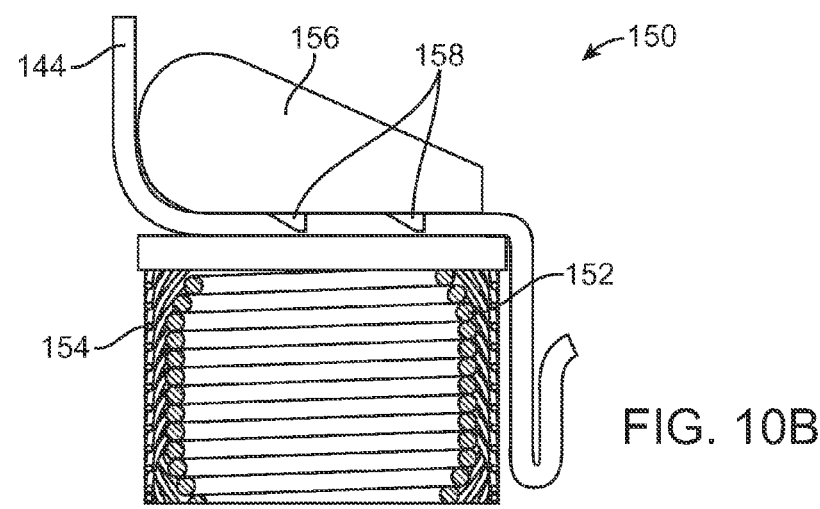

Referring now to FIGS. 10A and 10B, a further flexion restriction system 140 in accordance with the principles of the present invention will be described. As with all previously described systems, the system 140 comprises a pair of compliance members 142 attached to superior and inferior tether structures 144 and 146, respectively. The compliance members 142 each comprise a fixed tether connector 148 and an adjustable tether connector 150. The tether connectors 148 and 150 are joined by a coil spring 152 (best seen in FIG. 10B) which is enclosed within a textile sheath 154. The superior tether structure 144 is fixably connected to the fixed tether connector 148 on the left hand side compliance member 142, while the inferior tether structure 146 is fixedly connected to the fixed connector 148 on the right compliance member 142. Each of the adjustable tether connectors 150 includes a latch arm cam lock 156 which may be lifted or opened, as shown in FIG. 10A, to allow a free end of the tether structure 144 or 146 to be advanced therebeneath so that the tether can be tightened or cinched over an adjacent spinous process. Once the tether structure 144 or 146 has been sufficiently tightened, the latch arm 156 may be closed, as shown in FIG. 10B, to hold the tether structure 144 or 146 firmly in place. To prevent loosening, each latch arm cam lock 146 may be provided with surface textures or other gripping features such as spikes or chevrons 158.

Figure 11:
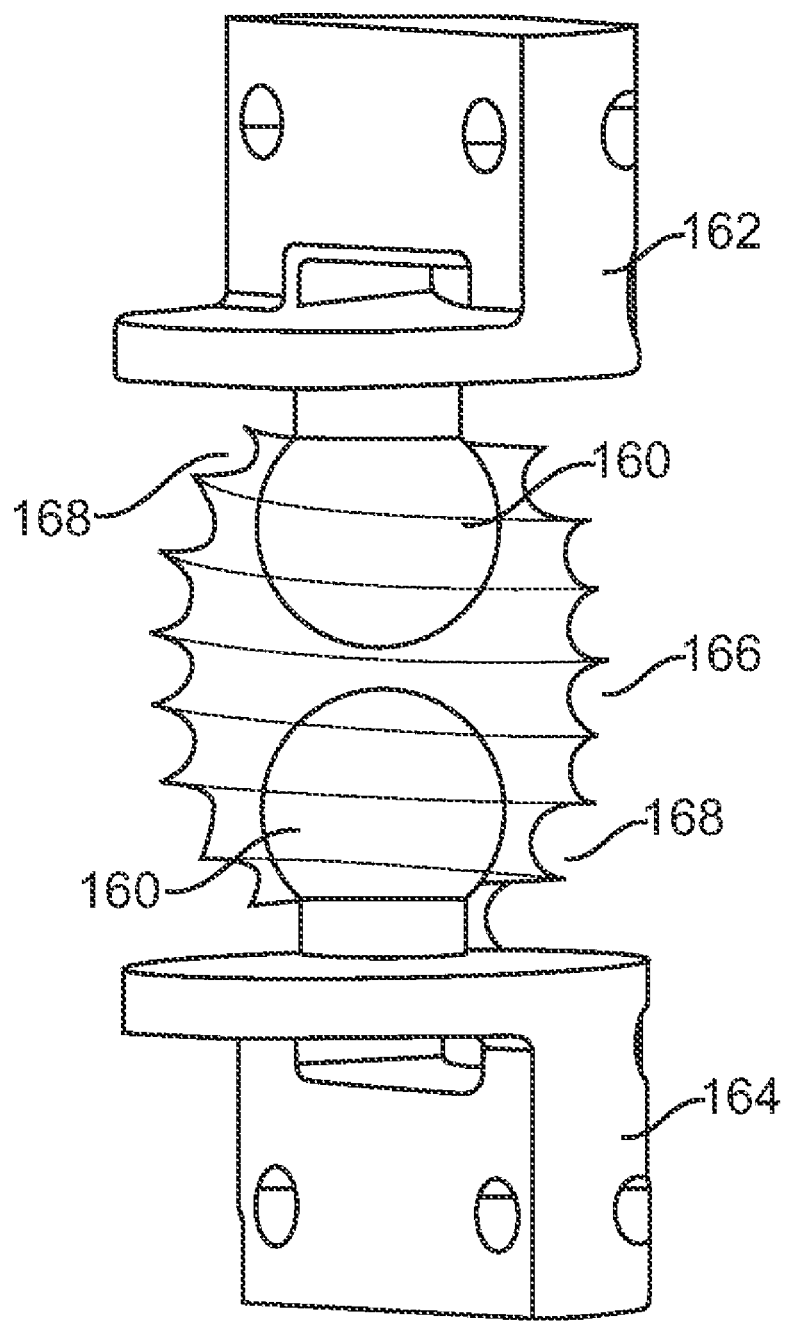
FIG. 11 illustrates a particular technique for connecting a coil spring tension member to upper and lower connector members.

In the embodiment of FIGS. 10A and 10B, the coil spring 152 may be secured to the fixed and adjustable tether connectors 148 and 150 by any conventional technique. In certain cases, however, it may be desirable to provide a pivotable or adjustable connection, as shown in FIG. 11. There, ball joints 160 may be formed on superior and inferior connectors 162 and 164, respectively. A coil spring 166 may have converging ends 168 which can be secured over the ball joints to provide a universal joint therebetween.

Figure 10C:
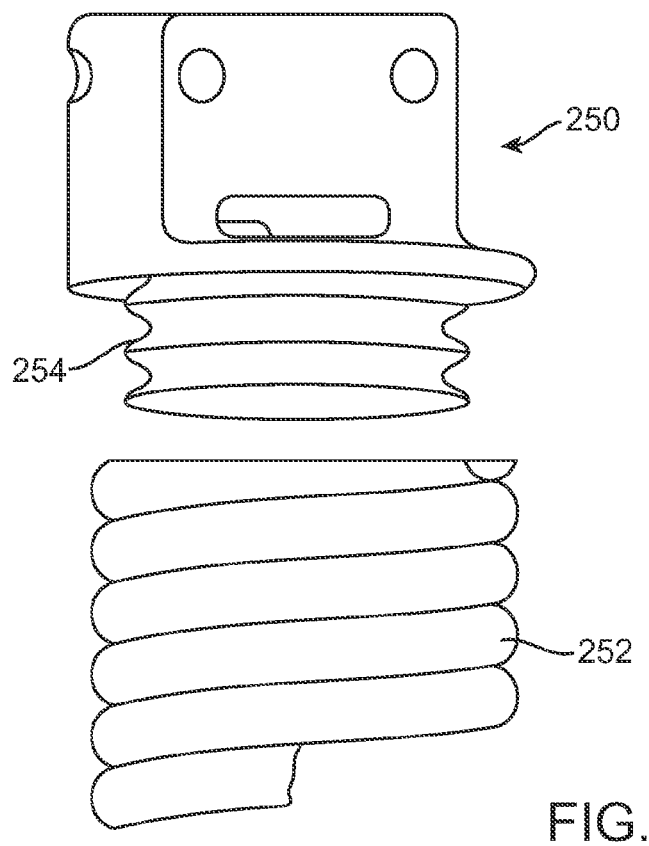
FIGS. 10C and 10D illustrate an alternative method for joining a coil spring tension member to a connector.
Figure 10D:
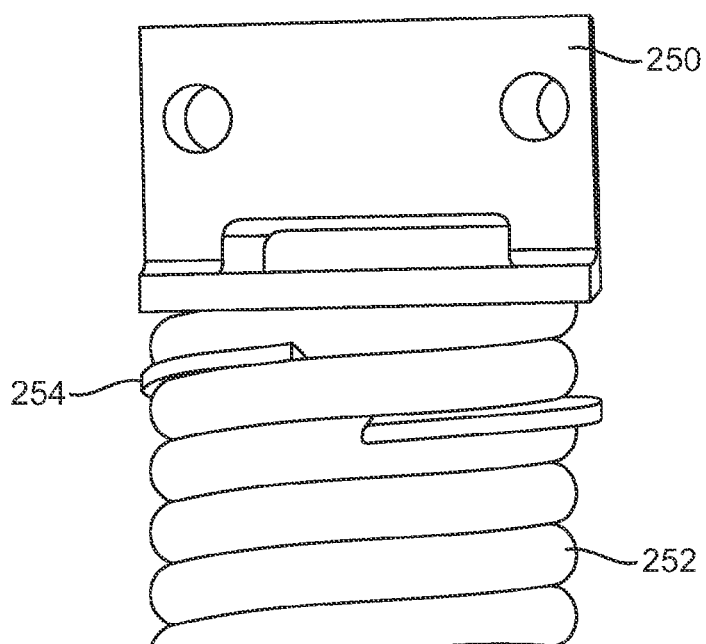

Coil spring tension members may be secured to both fixed and adjustable tether connectors, such as connectors 148 and 150 in FIGS. 10A and 10B, in a variety of ways. As shown in FIGS. 10C and 10D, a tether connector 250 may be attached to an end of a coil spring 252 using a threaded receiving component 254 which can be screwed in to the coil spring, as illustrated in FIG. 10D. The threaded receiving component 254 mates with the coil spring, typically by threadably engaging the internal grooves on the coil spring, thus evenly spreading the tension across the end of the spring. Optionally, or alternatively, the receiving component 254 can be welded in place, held in place by a suitable adhesive, or be held in place by various secondary fasteners, such as screws, rivits, or the like.

Figure 12A:
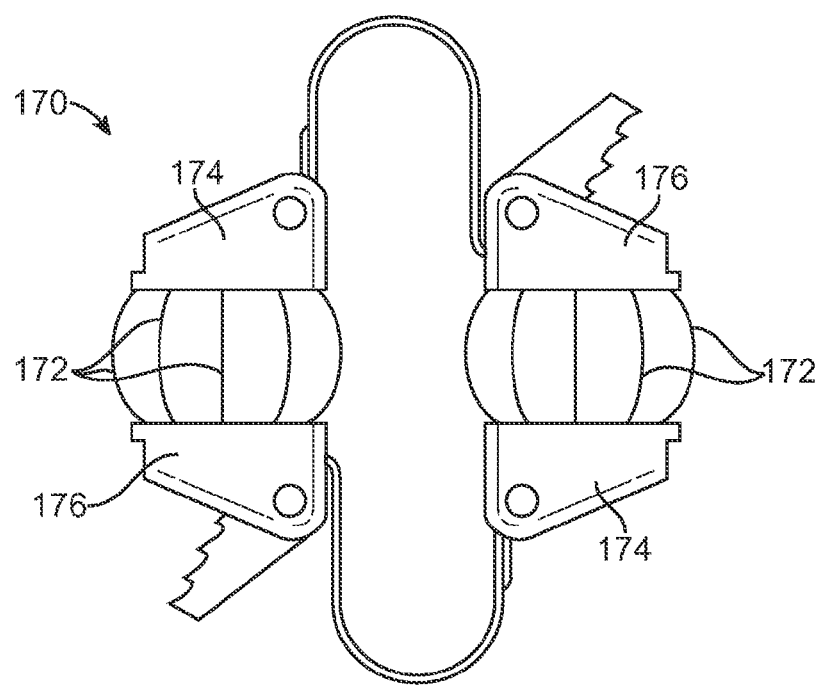
FIGS. 12A and 12B illustrate a constraint assembly similar to that shown in FIGS. 10A and 10B where the sheath contains elements which minimize sheath interaction with the tension element and/or limit the maximum elongation of the assembly under tension.
Figure 12B:
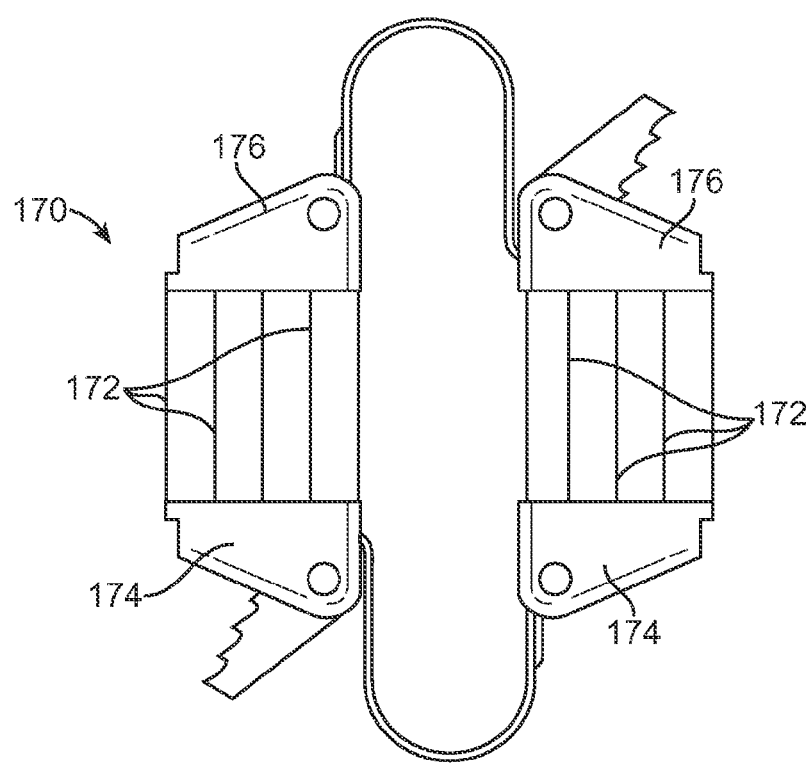

Referring now to FIGS. 12A and 12B, yet another alternative construction of a flexible restraint system 170 will be described. The flexible restraint system 170 may be identical in all respects to the flexible restraint system 140 as described previously. Instead of a mesh sheath, however, the flexible restraint system 170 includes a sheath having a plurality of battens or wires 172 which reduce interactions between the sheath and restraint system, as well as provide an axial constraint to limit the maximum axial separation of the fixed and adjustable tether connectors 174 and 176, respectively. As shown in FIG. 12A, the battens 172 are axially compressed so that they bow outwardly, distancing the sheath from the tensile member. In FIG. 12B, the fixed and adjustable tether connectors 174 and 176 have moved to their maximum axial separation, straightening the battens 172.

Figure 13A:
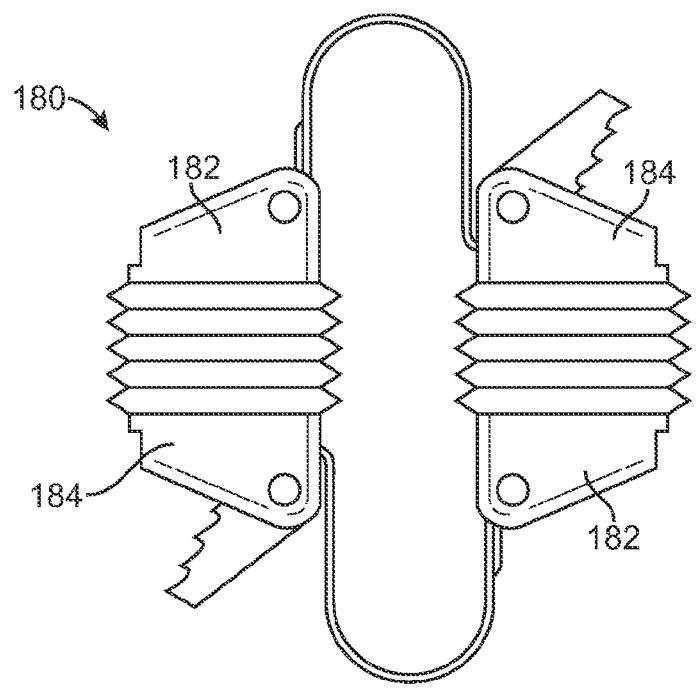
FIGS. 13A and 13B illustrate an accordion-type sheath which could potentially also limit maximum elongation.
Figure 13B:
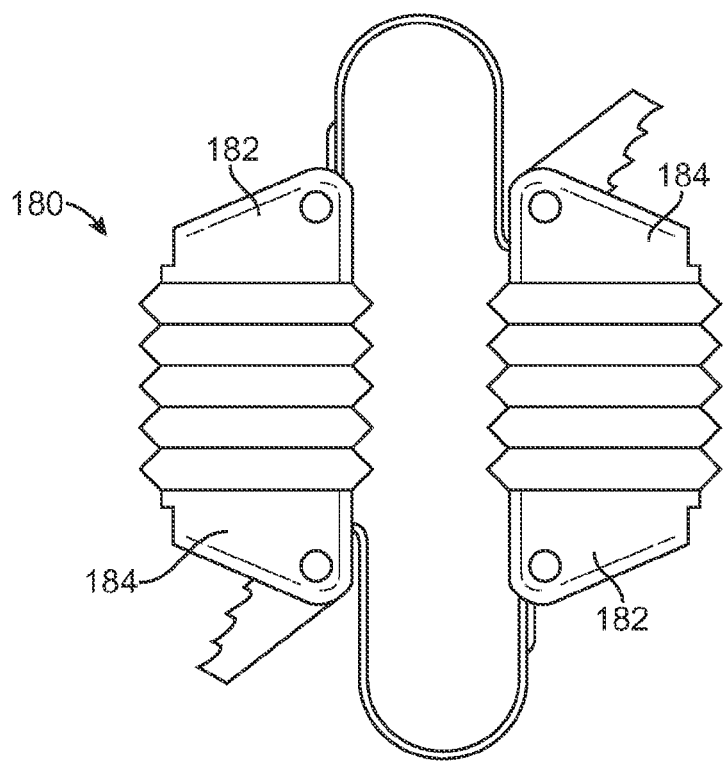

Referring now to FIGS. 13A and 13B, yet another flexible restraint system 180 constructed in accordance with the principles of the present invention will be described. The flexible restraint system 180 is similar to those of both systems 170 and 140, except that the sheath structure has an accordion fold to provide for lengthening and shortening together with the movement of fixed and adjustable tether connectors 182 and 184, respectively. The accordion folds both permit greater gross elongation of the sheath with lower material strains than in a purely cylindrical sheath and potentially reduce interaction between the sheath and tensile member. The sheath with the accordion fold may or may not act as a constraint on maximum elongation of the compliance members. The sheath could also be used with separate tension members for providing the maximum elongation limit.

Pre-tensioning or pre-loading of compliance members is illustrated in FIGS. 14A and 14B. In FIG. 14A, a compliance member 260 includes a spring compression member 262 placed in a housing 264 and a superior tether structure 266 which is secured to a piston 268 which is free to slide within an interior chamber 270 of the housing 264. The coil spring 262 is disposed between an upper surface of the piston 268 and the lower surface of the top end of the housing 260. If the coil spring 262 is sized so that it occupies the space between the piston and the top end of the housing without any compression, then the compliance member 260 will have no pre-tensioning or pre-loading. If, however, pre-tensioning is desired, the spring 262 will be chosen to be slightly longer than the distance between the piston and the top end of the housing so that the spring 262 is under compression even when there is no tension being placed on the superior tether 266 or the inferior tether 267. Note that the degree of pre-tensioning can be controlled by selecting the position of retaining shoulders 270 formed on the interior surface of the housing 264. The compliance member 260 will apply elastic resistance to spreading of tension members 266 and 267 as the spring compresses in the direction of the arrows.

An alternative compliance member 280 is illustrated in FIG. 14B. Compliance member 280 includes a tension spring member 282 received in the interior 284 of housing 286. A superior tether structure 288 is attached to an upper end of the housing 286 and an inferior tether structure 290 is attached to a piston 292 slidably received in the interior 284 of the housing. When tension is applied to the superior and inferior tether structures 288 and 290, tension will be transferred to the spring in the direction of the arrows which will elastically resist spreading apart of the tether structures.

Movement of the piston 292 is constrained by a shoulder 294 formed about the circumference of the interior 284. If the spring 282 is selected so that its length is equal to the length between the piston (when engaged against the shoulder 294) and the upper end of the interior 284, then there will be no pre-tensioning of the spring. If, however, the spring is selected so that it is shorter than the distance between the piston 292 and the upper end of the chamber 284, then the spring will be in tension at all times, even prior to elongation by placing a force between the tether structures. In this way, the initial displacement of the tether structures relative to each other will act to overcome the pre-tensioning force of the spring.

The effect of pre-tensioning on the kinematics of the compliance members is best understood with reference to FIGS. 15A and 15B. In FIG. 15A, the relationship between force F and displacement D for a compliance member without pre-tensioning is illustrated. Prior to displacement, when the displacement is zero, the spring force will be essentially zero. The spring force will increase linearly from zero depending on the spring constant k as illustrated. When the tension member 262 or 284 is pre-tensioned, however, the initial force imparted by the compliance member will be $F_0$ (greater than zero), as shown in FIG. 15B. The magnitude of $F_0$ is determined by the degree of pre-tensioning, typically being in the range from 0N to 50N, usually from 5N to 25N, for the compliance members herein. Once displacement begins, however, the increase in force ($F-F_0$) will be linear and again determined by the spring constant k.

Figure 16:
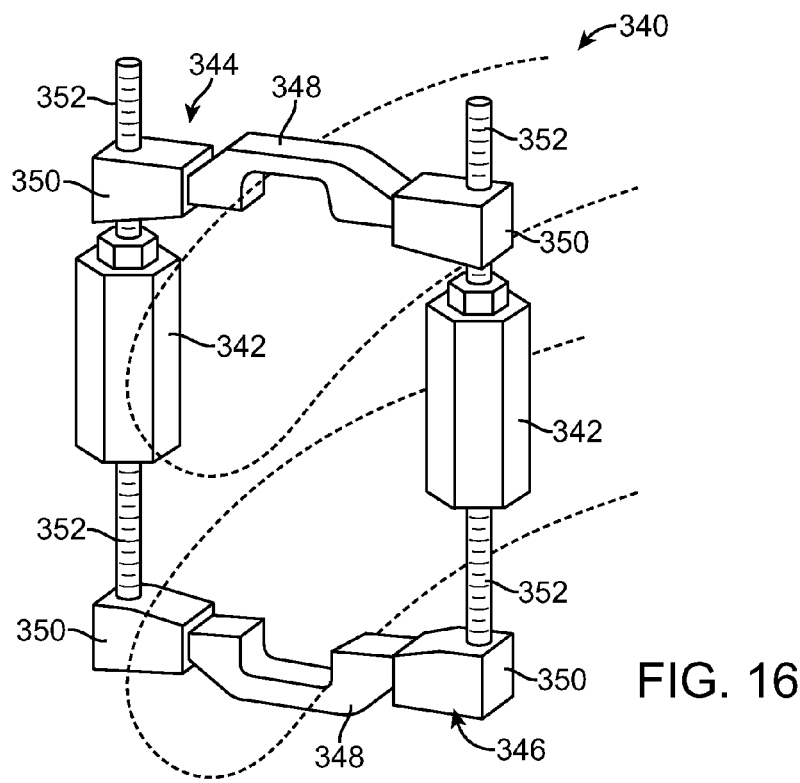
FIG. 16 illustrates a spinous process constraint structure incorporating a rigid frame work for coupling compliance members to adjacent spinous processes.

As illustrated thus far, spinous constraint structures of the present invention have generally included flexible, typically non-distensible, tethers or bands adjoining the superior and inferior ends of the compliance members. Instead of employing such flexible tether structures, the compliance members could be joined by a rigid frame structure 340, as illustrated in FIG. 16. For example, compliance members 342 could be joined to superior and inferior yokes 344 and 346, each of which include a central engagement member 348 for placement over the superior and inferior spinous processes. Optionally, the engagement members 348 could be pivotally attached between a pair of adjacent wing members 350. The wings members 350, in turn, could be coupled to the compliance members 342 using rods or posts 352, where the rods or posts 352 are optionally threaded to allow adjustment and tightening of the yokes 344 and 346 over the spinous processes. The compliance members 342 could have any of the tension members and coupling structures described previously in order to connect to the posts 352.

Figure 17:
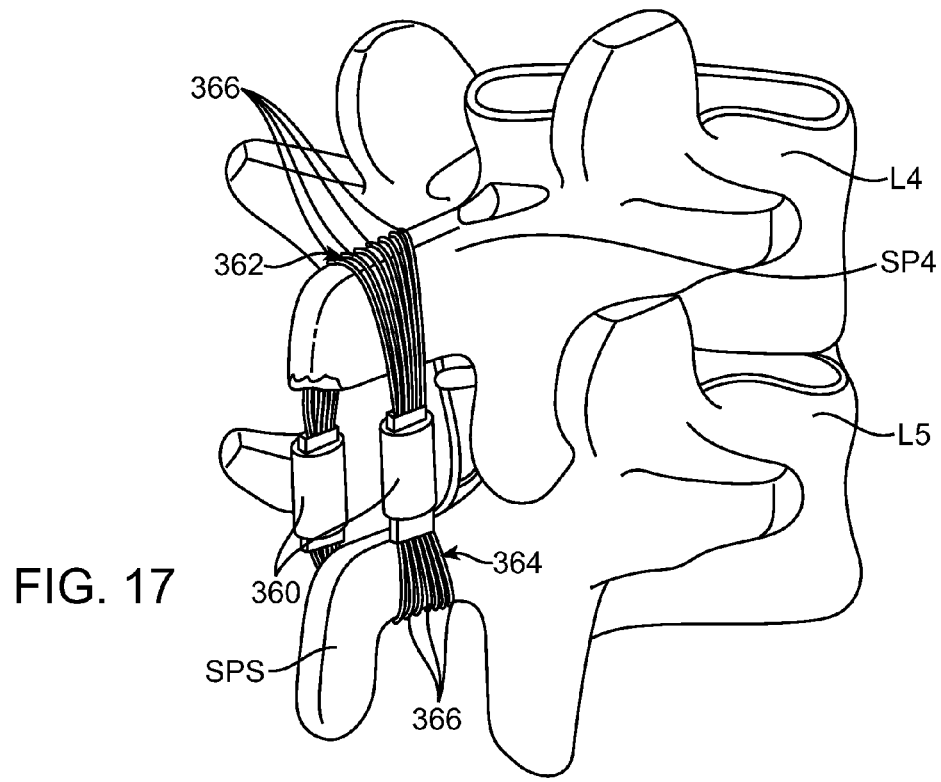
FIG. 17 illustrates a spinous process constraint structure having the superior and inferior tether structures each of which comprise a plurality of individual coupling elements.

Referring now to FIG. 17, as a further alternative to the tether structures which have been previously described, compliance members 360 could be joined by superior and inferior tether structures 362 and 364 each of which comprises a plurality of individual coupling elements 366. The individual coupling elements 366 could include filaments, strands, fibers, wires, small diameter cables, and the like, composed of polymers, metals, metal-polymer composites, and the like. Coupling elements could be simple constant diameter elongate elements, but could alternatively comprise regions of different characteristics, including elastic regions, spring-like regions, rigid regions, or the like. The individual fibers will typically be free to move relative to each other so that they independently function to couple the compliance members 360 together. In that way, should any of the coupling elements 366 fail, the remaining coupling elements would not be compromised. Alternatively, the individual coupling elements 366 could be woven or braided together along a portion of or their entire lengths. An advantage of the use of individual coupling elements is that the elements may spread and conform to the particular geometry of the spinous process providing a more stable connection. Certain embodiments, in the coupling elements could be composed entirely or in part of a material that promotes tissue ingrowth, such as tantalum.

Figure 18:
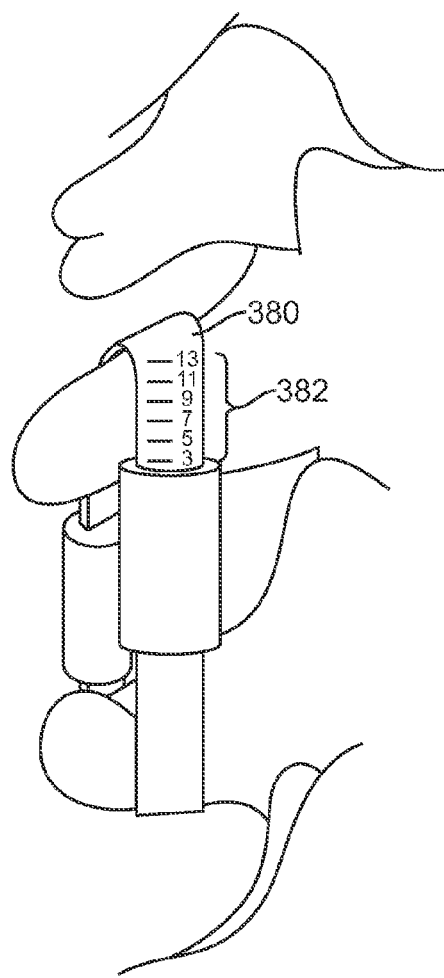
FIGS. 18 and 19 illustrate the use of indicators which provide readings of displacement and/or force between the compliance member and the associated tether, where the indicated information is useful in initial positioning and/or subsequent monitoring of the performance of the spinous process constraint system.

In some instances, it may be desirable to incorporate the ability to monitor displacement and/or tension force between the tether structures and the compliance members. As illustrated in FIG. 18, an upper tether member 380 can be provided with a scale or other indicia 382 that indicates the displacement or band length. Alternatively, the scale or indicia 382 could be calibrated to show displacement force.

Figure 19:
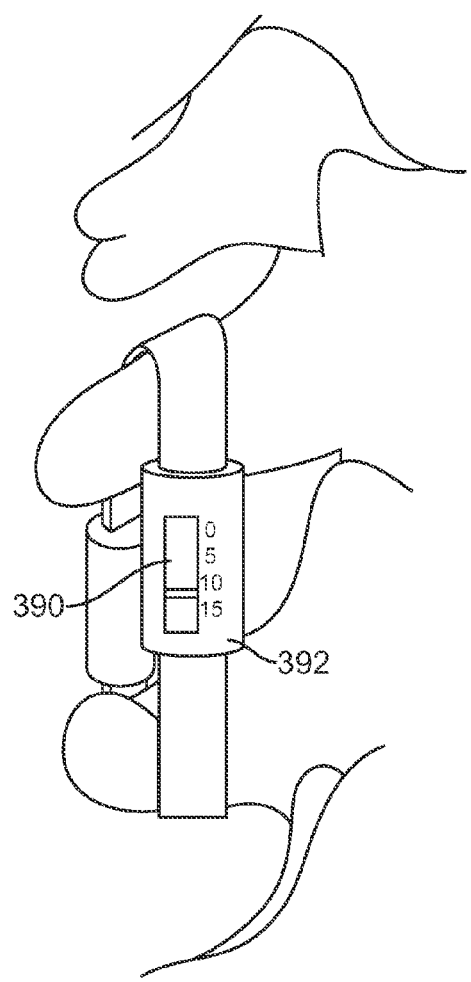

The displacement or force measurement could also be provided in an indicator window 390 in a compliance member 392, as shown in FIG. 19. Often, the indicia will be visible by the physician during the implantation procedure. Alternatively, the indicia could be transmitted for reading during implantation procedure and optionally after implantation. The indicia could be configured so that it is visible on imaging procedures, such as x-rays, MRI'S and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for restricting flexion of at least one spinal segment, said method comprising:
   implanting a constraining structure having a superior end coupled to a superior spinous process and an inferior end coupled to an inferior spinous process or a sacrum, wherein the constraining structure has an undeformed position and implanting comprises placing a superior tether structure over or through the superior spinous process and placing an inferior tether structure over or through the inferior spinous process or sacrum, wherein the tether structures are substantially non-distensible and joined by at least one compliance member which provides an elastic resistance to flexion; wherein the constraining structure provides the elastic resistance to flexion beyond a neutral position of the spinal segment in the range from 7.5 N/mm to 20 N/mm wherein the constraining structure elastically recovers its undeformed position when the spinal segment returns to its neutral position; and wherein the tethers of the constraining structure will experience a creep below 10% after one million cycles at typical physiologic loads.

2. A method as in claim 1, wherein the constraining structure provides a resistance to extension beyond the neutral position of the spinal segment below 3 N/mm.

3. A method as in claim 2, wherein the resistance to extension is below 0.5 N/mm.

4. A method as in claim 1, wherein the tether structures are joined by at least two compliance members which are placed on the right and left sides of a midline of the spinal segment.

5. A method as in claim 1, wherein the constraining structure is tightened over the spinous processes to apply a force to the spinous processes in the range from 1N to 25N before flexion while the spinal segment remains at a neutral position.

6. A method as in claim 1, wherein the constraining structure is pre-tensioned to provide an initial static resistance in the range from 5N to 25N which must be overcome before initiating deformation.

7. A method as in claim 1, wherein the creep is below 5%.

8. A method as in claim 7, wherein the creep is below 1%.

* * * * *